United States Patent [19]

Chupp

[11] 4,351,667

[45] Sep. 28, 1982

[54] HERBICIDAL TERTIARY 2-HALOACETAMIDES

[75] Inventor: John P. Chupp, Kirkwood, Mo.

[73] Assignee: Monsanto Company, St. Louis, Mo.

[21] Appl. No.: 31,087

[22] Filed: Apr. 18, 1979

Related U.S. Application Data

[63] Continuation-in-part of Ser. No. 897,472, Apr. 18, 1978, abandoned.

[51] Int. Cl.³ .................... A01N 37/18; C07C 103/37; C07C 121/48
[52] U.S. Cl. ........................................ 71/118; 71/105; 564/210; 564/152; 260/464
[58] Field of Search ................. 71/118, 105; 260/569, 260/464; 564/210, 152

[56] References Cited

U.S. PATENT DOCUMENTS 3,574,746  4/1971  Chupp .................................. 260/561
4,025,554  5/1977  Tournayre et al. ............ 260/562 A

*Primary Examiner*—Catherine L. Mills
*Attorney, Agent, or Firm*—William I. Andress; Howard C. Stanley

[57] ABSTRACT

The disclosure herein relates to tertiary 2-haloacetamides substituted on the amide nitrogen atom with certain 1-cycloalken-1-yl, alkoxymethyl, alkylthiomethyl or acetamidomethyl radicals. These acetamides are useful as herbicides.

45 Claims, No Drawings

HERBICIDAL TERTIARY 2-HALOACETAMIDES

This application is a continuation-in-part of Ser. No. 897,472, filed Apr. 18, 1978, now abandoned.

BACKGROUND OF THE INVENTION

1. Field of the Invention

This invention pertains to the field of tertiary 2-haloacetamides and their use in the agronomic arts, e.g., as herbicides.

2. Description of the Prior Art

It is known in the prior art to use various 2-haloacetamides as active ingredients in herbicides.

Among herbicidal acetamides of the prior art are those having a variety of substituents on the amide nitrogen atom including alkyl, cycloalkyl, alkenyl, cycloalkenyl, alkoxy, halogen, aryl, etc.

Illustrative of the 2-haloacetamides of the prior art are those disclosed in U.S. Pat. Nos. 3,495,967; 3,901,917; 3,819,661; 3,946,045; and 4,012,222. All of these patents disclose 2-haloacetamides having a heterocyclic radical and hydrogen or an aromatic or aliphatic radical attached to the amide nitrogen.

U.S. Pat. No. 2,864,683 discloses 2-haloacetamides having one or more hydrogen, alkyl, alkenyl, alkynyl or halogenated analogs thereof on the nitrogen atom. U.S. Pat. Nos. 2,863,752 (Re. 26,961), 3,442,945, and 3,547,620 exemplify 2-haloacetamides having phenyl or substituted phenyl and hydrogen, alkyl, alkenyl, alkynyl or oxaalkylene radicals attached to the amide nitrogen atom.

More relevant to the 2-haloacetamides of this invention are those disclosed in U.S. Pat. Nos. 3,574,746 and 3,586,496. The 2-haloacetamides of these patents are characterized in relevant part by N-substituents of a 1-cycloalken-1-yl radical (which may be further substituted) and another substituent, which may include an alkoxyalkyl radical having up to 8 carbon atoms. These products are prepared by haloacetylating an N-(alkoxyalkyl) cycloalkylidene amine. However, that process is only amenable to producing 2-haloacetamides containing N-alkoxyalkyl radicals having no less than 2 carbon atoms between the amide nitrogen and ether oxygen atoms. This is amply demonstrated by the fact that no N-alkoxymethyl-substituted compounds are exemplified in the '746 and '496 patents. The reason for this is simple, viz, the N-alkoxymethyl cycloalkylidene amines required as starting materials to produce the corresponding N-alkoxymethyl-N-(1-cycloalken-1-yl)-2-haloacetamides do not exist. Nor do secondary N-(alkoxymethyl)-N-(1-cycloalken-1-yl) amines exist. Moreover, the primary alkoxymethyl amines necessary to react with cycloalkanones to produce such imines also do not exist. These theoretical starting materials either cannot be prepared or are so unstable they exist only momentarily as transitory intermediates.

Therefore, no known process of the prior art is capable of producing the N-(alkoxymethyl)-N-(1-cycloalken-1-yl)-2-haloacetamides disclosed and claimed herein. These compounds have now been made available by a new process disclosed and claimed in U.S. Application Ser. No. 896,879 filed Apr. 17, 1978, now abandoned, and further discussed below in the Detailed Description of the Invention.

It is, therefore, an object of this invention to provide a new class of 2-haloacetamides.

It is a further object of this invention to provide herbicidal compositions containing said new 2-haloacetamides as the active ingredient.

Still another object of this invention is the provision of a process for controlling undesirable weeds associated with dicotyledon and moncotyledon crops. Particular advantage is shown by some of the new 2-haloacetamides with respect to control of especially troublesome weeds such as yellow nutsedge, green foxtail, barnyardgrass and johnsongrass, while maintaining crop safety. Of particular advantage is the selective control of grass weeds in corn by certain herbicide species of this invention.

SUMMARY OF THE INVENTION

The present invention relates to herbicidally active compounds, herbicidal compositions containing these compounds and herbicidal method of use of said compositions in agricultural crops, e.g., in dicotyledonous crops such as cotton, peanuts, sugarbeets and soybeans, and in monocotyledonous crops such as corn, wheat, sorghum and rice.

The herbicidal compounds of this invention are characterized by the formula

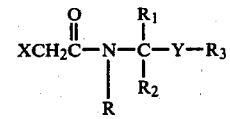

wherein

X is chlorine, bromine or iodine;

Y is O, S or $NR_4$

R is a $C_{5-7}$ 1-cycloalken-1-yl radical which may be substituted with from 1 to 6 halogen, alkyl, alkenyl, alkynyl, alkoxy, alkoxyalkyl, $C_{6-10}$ aryl or aralkyl groups;

$R_1$, $R_2$ and $R_4$ are independently hydrogen, $C_{1-6}$ alkyl, $C_{2-6}$ alkenyl, alkynyl or $C_{6-10}$ aryl or aralkyl and $R_3$ is $C_{1-6}$ acyl, $C_{1-18}$ alkyl, $C_{2-18}$ alkenyl, alkynyl, alkoxyalkyl or polyalkoxyalkyl, $C_{3-7}$ cycloalkyl or cycloalkylmethyl, $C_{6-10}$ aryl or aralkyl, or said $R_3$ groups substituted with $C_{1-6}$ alkyl, alkenyl or alkynyl, cyano, halo or nitro groups and when Y is $NR_4$, $R_3$ must be and $R_4$ can further be $C_{1-16}$ acyl, haloacyl or sulfonyl.

Within the above formula compounds of particular interest are those wherein X is chlorine, Y is oxygen, $R_1$ and $R_2$ are hydrogen, $R_3$ is $C_{1-6}$ alkyl and R is a $C_{5-7}$ 1-cycloalken-1-yl radical, particularly 1-cyclohexen-1-yl or $C_{1-6}$ alkyl-substituted and/or alkoxy-substituted homologs or analogs thereof and 1-cyclopenten-1-yl and $C_{1-6}$ alkyl- and/or alkoxy-substituted homologs or analogs thereof. Preferred members within these subgenera of compounds are N-(methoxymethyl)-N-(2,6-dimethyl-1-cyclohexen-1-yl)-2-chloroacetamide and the N-(ethoxymethyl), N-(propoxymethyl) and N-(butoxymethyl) homologs thereof, N-(ethoxymethyl)-N-(2,6-dimethyl-1-cyclopenten-1-yl)-2-chloroacetamide, N-(n-propoxymethyl)-N-(2,6-dimethyl-1-cyclopenten-1-yl)-2-chloroacetamide and other N-(alkoxyalkyl) homologs thereof.

The above compounds are used singly or in combination as the active ingredient(s) in herbicidal compositions to control undesirable vegetation in important crops.

DETAILED DESCRIPTION OF THE INVENTION

As indicated above, the new N-(alkoxymethyl)-N-(1-cycloalken-1-yl)-2-haloacetamides of this invention (defined above in Summary of the Invention) have been made available for the first time by a new process. The new process, in various embodiments discussed below, comprises converting a sec-2-haloacetamide of the formula

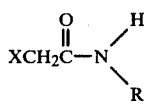

II to a stable anion thereof (negative charge on the nitrogen atom) under basic conditions by means of electrolysis or reaction with elemental metals, metal hydrides, hydroxides or alkoxides, and reacting said anion with a compound of the formula

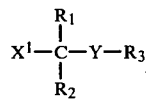

III wherein X, Y, R, $R_1$, $R_2$ and $R_3$ have meanings defined above and $X^1$ is a halogen, e.g., chlorine, bromine, iodine or a halogen equivalent such as p-toluenesulfonate, etc.

(A) A preferred embodiment of the above process utilizes a multiphase system employing a base sufficiently strong enough to react with the starting sec-amide optionally dissolved in an organic solvent, mainly at the interface, to produce incremental concentrations of amide anion. The presence of a phase transfer catalyst permits the so-formed amide anion to be transported via anion pair into the organic portion wherein most of the alkylating agent (i.e., compound of Formula III above) or activated olefin resides, and so react. The reaction will proceed without said catalyst, although yields are usually decreased, reaction times increased, and imidate by-product increased.

It will be understood that the weaker the acidity of the amide of Formula II, the stronger must be the base. Thus, e.g., weakly acidic amides such as the starting material for preparing N-(2,6-dimethyl-1-cyclohexen-1-yl)-N-(methoxymethyl)-2-chloracetamide (Example 1), namely, N-(2,6-dimethyl-1-cyclohexen-1-yl)-2-chloracetamide require in this embodiment, strong bases such as aqueous or solid sodium hydroxide or potassium hydroxide. Further, it is preferred when aqueous caustic is used that the solution be concentrated; (i.e., 20–50%).

On the other hand, in the alkylation of strongly acidic materials, a weaker base such as solid or aqueous sodium carbonate can be used to successfully generate amide anion and consequently effect alkylation.

It will be appreciated that the amide anion in this embodiment A will form an ion pair with the cation of the phase transfer catalyst. Therefore useful catalysts are those containing organic-soluble cations such as those enumerated in U.S. Pat. No. 3,992,432, including ammonium, phosphonium and sulfonium salts. Exemplary phase transfer catalysts include quaternary ammonium salts, e.g., aryl or aralkyl trialkyl ammonium halide salts such as benzyl triethyl ammonium bromide or chloride. Other phase transfer catalysts include the cyclic poly ethers which complex with the base cation and then pair with amide anion as counter ion for transport to the organic phase for alkylation. Exemplary of such catalysts would include "18-crown-6" cyclic ethers in combination with potassium hydroxide as base.

Other bases in this embodiment a dependent, however, on sec-amide acidity are, calcium hydroxide, trisodium phosphate, potassium carbonate, alkali metal hydroxides and carbonates, alkaline earth hydroxides.

(B) A second process embodiment for preparing the compounds of the present invention utilizes two different modifications to overcome by-product imidate formation (formed via O-alkylation). In the first, when small amounts of starting amide are used, i.e., up to about 50 g, phase transfer catalyst is increased to about 20–50% by weight of the amide charged, mixed with alkylating agent and the base added last. A second method, particularly useful for preparing large amounts of tertiary amide is to wash the reaction mixture (minus the base or aqueous phase) with dilute acid, preferably 5% HCl solution, wherein the imidate, but not the tertiary amide product, is converted to starting sec-amide. This mixture of amides can then be treated with fresh alkylating agent, catalyst and base to effect conversion of remaining sec-amide to tert-amide. It will be appreciated that such transformation of imidate to desired amide product can be effected in a recycling process either through a stepwise procedure, or by use of suitably designed equipment, as in a continuous or cascade process.

(C) Another process embodiment for preparing compounds of the present invention employs a reactive metallic organometallic or metal hydride to effect stoichiometric conversion of starting amide to amide anion. Exemplary is the addition of a dry ether or tetrahydrofuran solution of a secondary 2-chloroacetamide to an excess of potassium hydride, slurried in the same solvent; liberation of hydrogen occurs immediately, and in theory amount. The amide anion salt can then be reacted by addition of excess alkylating agent. Excess hydride is destroyed with water, and the tert-amide isolated as described in examples below. This embodiment has the advantages of minimizing imidate and diketopiperazine formation while preserving the alkylating agent which otherwise may be sensitive to aqueous base.

In considering embodiments of A, B and C, the ratios of reactants in these processes are not critical, but are dictated primarily by economic considerations and avoidance of unwanted by-products. Hence, large excesses or deficiencies of any component relative to another component should be avoided.

Inert solvents for use in the above process embodiments include, e.g., esters of alkanoic acids and alkanols such as ethyl acetate, etc., dichloromethane, benzene, chlorobenzene, tetrahydrofuran, dimethyl sulfoxide, toluene, diethyl ether, except that when aqueous bases are used in embodiments A and B the solvent should be appreciably water insoluble.

The process of this invention may be carried out at temperatures ranging from subzero to ambient or higher, e.g., from $-20°$ to $+110°$ C., but usually room temperature are sufficient, and desirable.

(D) Another process embodiment for producing compounds of this invention involves the generation of the secondary amide anion by electrolytic means. In electrolytic processes, the amide anion is generated directly at a suitable cathode. The resulting anion is alkylated with an appropriate compound of Formula III above, e.g., haloalkyl alkyl ethers such as chloromethyl methyl ether.

The above embodiments are exemplified in the specific working examples which follow.

EXAMPLE 1

This example exemplifies preferred embodiments (A) and (B) of the present process utilizing a multiphase system to generate a stable 2-haloacetamide anion and "alkylation" of same with a compound according to Formula III above in the presence of a phase-transfer catalyst to produce the corresponding stable tertiary 2-haloacetamide. Part (a) describes the preparation of the secondary 2-haloacetamide starting material and Part (b) describes the generation of the amide anion and alkylation thereof.

(a) A reaction vessel is charged with 11.3 parts of chloroacetyl chloride, 150 parts of chlorobenzene and 25 parts of N-2,6-dimethylcyclohexylidene amine. The reaction mixture is refluxed for several hours, cooled and filtered to obtain 13.5 parts of solid product, M.P. 114°–115° C.

Calc'd for $C_{10}H_{17}ONCl$ (percent): Cl,17.55; N, 6.93, Found: Cl,17.86; N, 7.02.

The product was identified as N-(2,6-dimethyl-1-cyclohexen-1-yl)-2-chloroacetamide.

(b) A mixture of 400 g. of the sec-amide produced above in 760 ml methylene chloride and 300 ml chloromethyl methyl ether were mixed with 2 g. benzyl triethyl ammonium bromide. The mixture was cooled to 10° C., then added in a thin stream over 0.5 hour to a vigorously stirred mixture of 1100 ml of 50% sodium hydroxide, 300 ml methylene chloride and 9 g. benzyl triethyl ammonium bromide contained in a 5-liter 4-necked round bottomed flask. Exterior cooling with an ice/acetone bath was necessary to maintain the temperature under 25° C. The mixture was stirred for an additional one hour. GLC showed 78% tertiary amide produced and 22% of corresponding O-alkylated by-product, viz., O-(methoxymethyl)-N-(1-cyclohexen-1-yl)-2-chloroacetimide. The imidate by-product was converted back to sec-amide starting material simply by washing the mixture with 500 ml of 5% HCl. To the washed mixture was added an additional 350 of 50% NaOH, 120 ml of chloromethyl methyl ether and 5 g. of the quaternary ammonium phase-transfer catalyst. After separation of layers and additional water washing, the product was filtered through clay; methylene chloride solvent was evaporated and the residue treated to 85° C. (0.5 mm), then filtered through clay to purify the product. The product was recovered in about 99% yield and had a boiling point of 127° (0.15 mm).

| Empirical Formula | Analysis | | |
|---|---|---|---|
| | Element | Calculated | Found |
| $C_{12}H_{20}ClNO_2$ | C | 58.65 | 58.48 |
| | H | 8.20 | 8.22 |
| | N | 5.70 | 5.62 |

The product was identified as N-(2,6-dimethyl-1-cyclohexen-1-yl)-N-(methoxymethyl)-2-chloroacetamide.

The above process in Part (b) may be performed without HCl regeneration of sec-amide from the imidate when lesser quantities, i.e., up to 50 g. of the sec-amide are used, the catalyst concentration is increased up to as much as 20–50% of the amount of sec-amide used and the base, NaOH, is added last, all at once.

Structure proof of the products obtained in this and the following examples was afforded by mass spectroscopy, nuclear magnetic resonance and elemental analysis.

EXAMPLE 2

This examples describes the preparation of N-(ethoxymethyl)-N-(2,6-dimethyl-1-cyclopenten-1-yl)-2-chloroacetamide.

N-(2,6-dimethyl-1-cyclopenten-1-yl)-2-chloroacetamide (4 g, 0.021 mole), chloromethyl ethyl ether, 4.5 g, benzyl triethylammonium bromide, 2.0 g, (phase transfer catalyst and 100 ml methylene chloride ($CH_2Cl_2$) were charged to a 500 ml round bottom flask with magnetic stirrer. Fifteen (15) grams sodium hydroxide (50%) were added all at once; exotherm to 37°. with formation of white paste. The mixture was stirred one hour. Water was added and a layer of $CH_2Cl_2$ separated; solvent was removed in vacuo leaving a light-amber oil which was taken up in ether and washed with water. Ether layer dried over $MgSO_4$, filtered and solvent removed in vacuo leaving 4.8 g amber oil which was kugelrohred at 137° at 0.05 mm Hg to give 3.9 g of light-yellow oil. Yield 76%.

Calc'd for $C_{12}H_{20}ClNO_2$ (percent): C, 58.65; H, 8.20; N, 5.70, Found: C, 59.17; H, 8.37; N, 5.43.

EXAMPLE 3

This example describes the preparation of N-(n-propoxymethyl)-N-(2,5-dimethyl-1-cyclopenten-1-yl)-2-chloroacetacetamide.

To 4.0 g (0.021 mole) of N-(2,5-dimethyl-1-cyclopenten-1-yl)-2-chloroacetamide, 2.0 g benzyl triethylammonium bromide and 75 ml $CH_2Cl_2$ was added all at once, 15 g of 50% NaOH with exotherm to 40° and salt formation. The mixture was stirred one hour and layers separated; the $CH_2Cl_2$ layer removed in vacuo leaving an oil which was kugelrohred at 140° at 0.05 mm Hg to give 4.1 g oil. Yield 75%.

Calc'd for $C_{13}H_{22}ClNO_2$ (percent): C, 60.11; H, 8.54; N, 5.39, Found: C, 59.21; H, 8.56; N, 5.10.

EXAMPLE 4

To 2.2 g (0.01 mole) of N-(2-ethyl-6-methyl-1-cyclohexen-1-yl)-2-chloroacetamide, 3.0 g chloromethyl ethyl ether, 1.1 g benzyl triethylammonium bromide and 50 ml $CH_2Cl_2$ was added all at once 10 g of 50% NaOH; exotherm occurred with formation of white paste-like material, which was stirred 2 hours. Water was added and $CH_2Cl_2$ layer separated and dried over $MgSO_4$, then filtered and solvent removed in vacuo, leaving 4.3 g yellow oil which was kugelrohred at 123° at 0.05 mm Hg to give 2.4 g of clear colorless oil. Yield 88%.

Calc'd for $C_{14}H_{24}ClNO_2$ (percent): C, 61.42; H, 8.84; N, 5.12; Found: C, 61.38; H, 8.84; N, 5.07.

The product was identified as N-(ethoxymethyl)-N-(2-ethyl-6-methyl-1-cyclohexen-1-yl)-2-chloroacetamide.

EXAMPLE 5

N-(2-methyl-6-ethyl-1-cyclohexen-1-yl)-2-chloroacetamide, 2.2 g (0.0102 mole), 3.0 g (0.032 mol) of chloromethyl ethyl ether, and 1.0 g of benzyl triethylammonium bromide were charged to a 100 ml round bottom flask with 50 ml $CH_2Cl_2$ and magnetic stirrer and 4.0 g NaOH (50%) were added all at once. Exotherm to reflux temperature for several minutes and stirred 1 hour. G.L.C. analysis showed a mixture of the isomeric sec-amide starting materials of Example 4 and this Example 5, the tert-amide product of Example 4 and its N-(ethoxymethyl)-N-(2-methyl-6-ethyl-1-cyclohexen-1-yl)-2-chloroacetamide isomer.

EXAMPLE 6

This example describes the preparation and separation of the isomeric tert-amides prepared in Examples 4 and 5.

To 2.5 g (0.012 mole) of N-(2-methyl-6-ethyl-1-cyclohexen-1-yl) acetamide, 4.8 g (0.05 mole) chloromethyl ethyl ether, 1.2 g benzyl triethylammonium bromide and 80 ml $CH_2Cl_2$ was added 10 g 50% NaOH all at once; exotherm to reflux temperature of $CH_2Cl_2$ and formation of thick white paste which was stirred one hour. GLC analysis of the mixture showed 80% of the product of Example 5, 5.5% of the starting sec-amide of Example 5, 3.6% of the starting sec-amide material of Example 4 and 11% other product. Water was added and the mixture stirred; $CH_2Cl_2$ layer separated and solvent removed in vacuo leaving an oil which was taken up in ether, washed with water, dried over $MgSO_4$, filtered and the solvent removed in vacuo leaving 3.2 g of light-yellow oil which was combined with 2.5 g of the product of Example 5; this mixture separated by HPLC. The first peak off was unsymmetrical containing an isomeric mixture of the tertiary-2-haloamides produced in Examples 4 and 5. NMR analysis indicated in a first fraction 1.2 g of both isomers of said tertiary-2-haloamides; 1.5 g of the tert-amide isomer of Example 5 in a second fraction and 0.5 g in a third fraction; while fourth and fifth fractions contained, respectively, a small quantity of the starting sec-amides of Examples 4 and 5.

The first and second fractions were chromatographed a second time using a 5% ethylacetate/petroleum ether elutant. After 5.75 hours a very broad peak developed; after 1.5 hour the elutant was increased to 20% ethyl acetate and the peak sharpened thereafter. A first and second fraction each showed an isomeric mixture of the tertiary amide products of Examples 4 and 5, a third fraction showed pure product of Example 5. Evaporation of the latter fraction gave an oil which was kugelrohred at 125° C. at 0.05 mm Hg to give 2.0 g of clear colorless oil.

Calc'd for $C_{14}H_{24}ClNO_2$ (percent): C, 61.42; H, 8.84; N, 5.12, Found: C, 61.33; H, 8.84; N, 5.09.
The product was thus identified as N-(ethoxymethyl)-N-(2-methyl-6-ethyl-1-cyclohexen-1-yl)-2-chloroacetamide.

EXAMPLE 7

This example illustrates the above process embodiment C utilizing a metal hydride as the sec-amide anion generator to produce the same t-amide product produced in Example 1.

Potassium hydride (KH) in mineral oil (0.056 mol, 10.2 g) was washed 3 times with petroleum ether; after each wash most of the solvent was removed through a flexible needle under nitrogen pressure. N-(2,6-dimethyl-1-cyclohexen-1-yl)-2-chloroacetamide (0.056 mol, 11.3 g) in 300 ml ether was added dropwise rapidly with stirring over 0.5 hour, with the theory hydrogen evolved measured by a wet test meter. Freshly-distilled chloromethyl methyl ether (0.18 mol, 15 g) in 200 ml ether was added dropwise and stirred for 50 minutes to insure full precipitation of potassium chloride. Wet ether added cautiously. When all excess KH had reacted, 300 ml of water were added. The ether was extracted, dried over $MgSO_4$, filtered and removed under vacuum leaving 6.3 g of oil which was vacuum distilled to give 4.2 g of oil, b.p. 127° C. (0.15 mm).

EXAMPLE 8

Following the same general procedure described in Example 7, but substituting chloromethyl methyl thioether ($ClCH_2SCH_3$) as the alkylating agent, an oil was obtained in 11% yield.

Calc'd for $C_{12}H_{20}ClNOS$ (percent): C, 55.05; H, 7.70; N, 5.35, Found: C, 54.88; H, 7.75; N, 5.29.
The product was identified as N-(methylthiomethyl)-N-(2,6-dimethyl-1-cyclohexen-1-yl)-2-chloroacetamide.

In similar manner, when chloromethyl phenyl thioether is used as the alkylating agent, one obtains the corresponding tertiary amide, N-(phenylthiomethyl)-N-(2,6-dimethyl-1-cyclohexen-1-yl)-2-chloroacetamide.

EXAMPLE 9

Potassium hydride (0.056 mol) in petroleum ether and N-(2,6-dimethyl-1-cyclohexen-1-yl)-2-chloroacetamide (0.05 mol) dissolved in 300 ml of ether were mixed and refluxed at 30° with evolution of about 2–2.5 l of hydrogen. Freshly prepared chloroethyl methyl ether (0.085 mole) was added with stirring (strong exotherm) over a 15 minute period with precipitation of a white solid, m.p. 76°–79° C. in 23% yield.

Calc'd for $C_{13}H_{22}ClNO_2$ (percent): C, 60.11; H, 8.54; N, 5.39; Found: C, 59.96; H, 8.57; N, 5.44.
The product was identified as N-(1-methoxy-1-ethyl)-N-(2,6-dimethyl-1-cyclohexen-1-yl)-2-chloroacetamide.

EXAMPLE 10

This example illustrates sec-amide anion formation by direct electrochemical reduction and alkylation of the anion.

The electrolyses were performed in an all-glass H-cell of conventional design with a medium porosity sintered glass frit separating the anode and cathode compartments. The volume of the cathode compartment was approximately 70 ml and that of the anode compartment was approximately 30 ml. The cathode was a 45-mesh platinum gauze rectangle with a geometrical area of approximately 12 $cm^2$. The anode was a graphite rod with a diameter of 6 mm. A silver wire reference electrode extended into the cathode compartment and was contained and separated from the catholyte by a fritted compartment.

The solvent may be acetonitrile, N,N-dimethylformamide or other aprotic dipolar solvents suitable for electrochemical reductions which contain a sufficient concentration of a supporting electrolyte salt to render it sufficiently conducting. The supporting electrolytes include, but are not limited to, alkali metal perchlorates, fluoborates and halides and tetraalkylammonium perchlorates, fluoborates and halides.

The solvent-supporting electrolyte mixture was charged with both the cathode and anode compartments, and the catholyte was purged with an inert gas such as nitrogen or argon to remove dissolved oxygen. To the catholyte was added the secondary α-chloroacetamide and the electrolysis was initiated. The electrolysis was carried out in a controlled potential mode using a Princeton Applied Research model 173 potentiostat. The cathode potential relative to the silver reference electrode was maintained sufficiently negative to reduce the amide, as evidenced by hydrogen evolution at the cathode. Upon completion of the electrolysis, a chloromethyl alkyl ether was added to alkylate the amide anion generated during the electrolysis. The chloromethyl ether may not be present in significant concentrations during the electrolysis since it is reduced in preference to the amide. In cases where alkylation of the amide anion by neutral α-chloroacetamide is a problem, the yield of desired product may be improved by adding the alkylating agent during the electrolysis in proportion to the amount of current passed.

As a specific example, 0.40 grams of N-(2,6-dimethyl-1-cyclohexen-1-yl)-2-chloroacetamide was electrolyzed in acetonitrile which was 0.1 M in sodium perchlorate. The cathode potential was maintained at $-2.0$ V vs. the Ag reference electrode. After passing 193 coulombs of charge, 0.21 g of chloromethyl ethyl ether was added to the catholyte and allowed to stir for one-half ($\frac{1}{2}$) hour.

The catholyte was separated, and most of the acetonitrile was removed under reduced pressure. Water was added to the residue, and the aqueous solution was extracted with 150 ml of ethyl ether. The ether solution was washed with water and saturated sodium chloride solution and dried over anhydrous magnesium sulfate. The mixture was filtered and ether was removed from the filtrate under reduced pressure to yield a clear oil. Gas chromatographic analysis of the reaction mixture indicates 16% secondary amide, 36.5% desired tertiary amide, i.e., N-(ethoxymethyl)-N-(2,6-dimethyl-1-cyclohexen-1-yl)-2-chloroacetamide, and 44% N,N'-bis(2,6-dimethyl-1-cyclohexenyl) piperazine-2,5-dione, the product resulting from self-alkylation. Optimization of this procedure would increase yield of tert-amide product and decrease undesired by-products.

EXAMPLES 11–68

Following the same general processes described in Examples 1–10, but substituting the appropriate starting materials and reaction conditions, other exemplary tertiary 2-haloacetamide compounds according to Formula I above are prepared from the corresponding sec-amide anion and the same or equivalent anion generators, alkylating agents, solvents and/or phase-transfer catalysts. Typical of such compounds according to this invention which are prepared according to the above processes are shown in Table 1 together with certain of their physical properties.

TABLE I

| Example No. | Compound | Empirical Formula | B.P. °C. (mm Hg) | Element | Analysis Calculated | Found |
|---|---|---|---|---|---|---|
| 11 | N—(methoxymethyl)-N—(2-methyl-1-cyclohexen-1-yl)-2-chloroacetamide | $C_{11}H_{18}ClNO_2$ | 29–31 (m.p) | C H N | 57.02 7.83 6.04 | 56.86 7.86 5.96 |
| 12 | N—(isobutoxymethyl)-N—(2,6-dimethyl-1-cyclohexen-1-yl)-2-chloroacetamide | $C_{15}H_{26}ClNO_2$ | 120 (0.1) | C H N | 62.59 9.10 4.87 | 62.33 9.16 4.78 |
| 13 | N—(butoxymethyl)-N—(2,6-dimethyl-1-cyclohexen-1-yl)-2-chloroacetamide | $C_{15}H_{26}ClNO_2$ | 132 (0.05) | C H N | 62.59 12.33 4.87 | 62.39 12.16 4.95 |
| 14 | N—(methoxymethyl)-N—(2-sec-butyl-1-cyclohexen-1-yl)-2-chloroacetamide | $C_{14}H_{24}ClNO_2$ | 125 (0.05) | C H N | 61.41 8.84 5.12 | 61.52 8.86 5.11 |
| 15 | N—(propoxymethyl)-N—(2,6-dimethyl-1-cyclohexen-1-yl)-2-chloroacetamide | $C_{14}H_{24}ClNO_2$ | 115 (0.05) | C H N | 61.41 8.84 5.12 | 61.51 8.84 5.18 |
| 16 | N—(methoxymethyl)-N—(2-ethyl-1-cyclohexen-1-yl)-2-chloroacetamide | $C_{12}H_{20}ClNO_2$ | 117 (0.05) | C H N | 58.65 8.20 5.70 | 58.75 8.29 5.66 |
| 17 | N—(allyloxymethyl)-N—(2,6-dimethyl-1-cyclohexen-1-yl)-2-chloroacetamide | $C_{14}H_{22}ClNO_2$ | 129 (0.05) | C H N | 61.87 8.16 5.15 | 61.69 8.19 5.12 |
| 18 | N—(isopropoxymethyl)-N—(2,6-dimethyl-1-cyclohexen-1-yl)-2-chloroacetamide | $C_{14}H_{24}ClNO_2$ | 115 (0.05) | C H N | 61.41 8.84 5.12 | 61.24 8.86 5.10 |
| 19 | N—(acetamidomethyl)-N—(2,6-dimethyl-1-cyclohexen-1-yl)-2-chloroacetamide | $C_{13}H_{21}ClN_2O_2$ | 110–112 (m.p.) | C H N | 57.24 7.76 10.27 | 57.26 7.76 10.28 |
| 20 | N—(propargyloxymethyl)-N—(2,6-dimethyl-1-cyclohexen-1-yl)-2-chloroacetamide | $C_{14}H_{20}ClNO_2$ | 150 (0.05) | C H N | 62.33 7.47 5.79 | 62.33 7.48 5.75 |
| 21 | N—(sec-butoxymethyl)-N—(2,6-dimethyl-1-cyclohexen-1-yl)-2-chloroacetamide | $C_{15}H_{26}ClNO_2$ | 133 (0.05) | C H N | 62.59 9.10 4.87 | 62.44 9.13 4.82 |
| 22 | N—(2-chloro-1-ethoxymethyl)-N—(2,6-dimethyl-1-cyclohexen-1-yl)-2-chloroacetamide | $C_{13}H_{21}Cl_2NO_2$ | 150 (0.05) | C H N | 53.07 7.19 4.76 | 52.94 7.25 4.68 |
| 23 | N—(1-but-2-enoxymethyl)-N—(2,6-dimethyl-1-cyclohexen-1-yl)-2-chloroacetamide | $C_{16}H_{22}ClNO$ | 111–113 (m.p.) | C H N | 63.04 8.46 4.90 | 62.86 8.54 4.81 |
| 24 | N—(t-butoxymethyl)-N—(2,6-dimethyl-1-cyclohexen-1-yl)-2-chloroacetamide | $C_{15}H_{26}ClNO_2$ | 120 (0.05) | C H N | 62.59 9.10 4.87 | 62.38 9.10 4.83 |
| 25 | N—(methoxymethyl)-N—(2-isopropyl-1-cyclohexen-1-yl)-2-chloroacetamide | $C_{13}H_{22}ClNO_2$ | 120 (0.05) | C H N | 60.11 8.54 5.39 | 60.43 8.71 5.15 |
| 26 | N—(propoxymethyl)-N—[2-(1-methylpropyl)-1-cyclohexen-1-yl]-2-chloroacetamide | $C_{16}H_{28}ClNO_2$ | 136 (0.05) | C H N | 63.66 9.35 4.64 | 63.75 9.42 4.61 |

TABLE I-continued

| Example No. | Compound | Empirical Formula | B.P. °C. (mm Hg) | Element | Analysis Calculated | Found |
|---|---|---|---|---|---|---|
| 27 | N—(allyloxymethyl)-N—(2-ethyl-1-cyclohexen-1-yl)-2-chloroacetamide | $C_{14}H_{22}ClNO_2$ | 124 (0.05) | C H N | 61.87 8.16 5.15 | 61.88 8.17 5.15 |
| 28 | N—(ethoxyethoxymethyl)-N—(2,6-dimethyl-1-cyclohexen-1-yl)-2-chloroacetamide | $C_{15}H_{26}ClNO_3$ | Oil | C H N | 59.30 8.63 4.61 | 59.20 8.63 4.61 |
| 29 | N—(butoxymethyl)-N—(2-methyl-1-cyclohexen-1-yl)-2-chloro-acetamide | $C_{14}H_{24}ClNO_2$ | 132 (0.05) | C H N | 61.41 8.81 5.12 | 62.43 9.12 5.85 |
| 30 | N—(methoxyethoxymethyl)-N—(2,6-dimethyl-1-cyclohexen-1-yl)-2-chloroacetamide | $C_{14}H_{24}ClNO_3$ | 140 (0.05) | C H N | 58.02 8.35 4.83 | 57.84 8.41 4.80 |
| 31 | N—(3,3-dichloro-2-propenoxymethyl)-N—(2,6-dimethyl-1-cyclohexen-1-yl)-2-chloro-acetamide | $C_{14}H_{20}Cl_3NO_2$ | 173 (0.25) | C H N | 49.36 5.92 4.11 | 49.17 5.95 4.09 |
| 32 | N—(3-chloro-2-propenoxymethyl)-N—(2,6-diemthyl-1-cyclohexen-1-yl)-2-chloroacetamide | $C_{14}H_{20}Cl_2NO_2$ | 159 (0.05) | C H N | 54.91 6.91 4.57 | 54.91 6.91 4.56 |
| 33 | N—(2,3,3-trichloro-2-propenoxymethyl)-N—(2,6-dimethyl-1-cyclohexen-1-yl)-2-chloroacetamide | $C_{14}H_{19}Cl_4NO_2$ | 173 (0.1) | C H N | 44.83 5.11 3.73 | 44.78 5.14 3.71 |
| 34 | N—(2,3-dichloro-2-propenoxymethyl)-N—(2,6-dimethyl-1-cyclohexen-1-yl)-2-chloro-acetamide | $C_{14}H_{20}Cl_3NO_2$ | 166 (0.05) | C H N | 49.36 5.92 4.11 | 49.69 6.28 4.13 |
| 35 | N—(2-chloro-2-propenoxymethyl)-N—(2,6-dimethyl-1-cyclohexen-1-yl)-2-chloro-acetamide | $C_{19}H_{21}Cl_2NO_2$ | 159 | C H N | 54.91 6.91 4.57 | 54.86 6.92 4.56 |
| 36 | N—(isobutoxymethyl)-N—(1-cyclohexen-1-yl)-2-chloroacetamide | $C_{13}H_{22}ClNO_2$ | 120 (0.05) | C H N | 60.11 8.54 5.39 | 59.98 8.55 5.38 |
| 37 | N—(methallyloxymethyl)-N—(2,6-dimethyl-1-cyclohexen-1-yl)-2-chloroacetamide | $C_{15}H_{24}ClNO_2$ | 128 (0.05) | C H N | 63.04 8.46 49.90 | 62.89 8.45 4.83 |
| 38 | N—(methoxymethyl)-N—(2,6-diethyl-1-cyclohexen-1-yl)-2-chloroacetamide | $C_{14}H_{24}ClNO_2$ | | C H N | 61.41 8.84 5.12 | 61.42 8.87 5.09 |
| 39 | N—(ethoxymethyl)-N—(2,6-diethyl-1-cyclohexen-1-yl)-2-chloroacetamide | $C_{15}H_{26}ClNO_2$ | 150 (0.05) | C H N | 62.59 9.11 4.87 | 62.44 9.10 4.82 |
| 40 | N—(ethoxymethyl)-N—(2-ethyl-6-t-butyl-1-cyclohexen-1-yl)-2-chloroacetamide | $C_{16}H_{28}ClNO_2$ | 140 (0.05) | C H N | 63.66 9.35 4.64 | 63.47 9.35 4.60 |
| 41 | N—(ethoxymethyl)-N—(2-iso-propyl-1-cyclohexen-1-yl)-2-chloroacetamide | $C_{14}H_{24}ClNO_2$ | 126 (0.05) | C H N | 61.41 8.84 5.12 | 61.25 8.87 5.11 |
| 42 | N—(methoxymethyl)-N—(2-methyl-6-ethyl-1-cyclohexen-1-yl)-2-chloroacetamide | $C_{13}H_{22}ClNO_2$ | 130 (0.05) | C H N | 60.11 8.54 5.39 | 60.00 8.57 5.33 |
| 43 | N—(methoxymethyl)-N—(2-ethyl-6-methyl-1-cyclohexen-1-yl)-2-chloroacetamide | $C_{13}H_{22}ClNO_2$ | 130 (0.05) | C H N | 60.11 8.54 5.39 | 60.08 8.54 5.39 |
| 44 | N—(ethoxymethyl)-N—(1-ethyl-1-cyclohexen-1-yl)-2-chloroacetamide | $C_{13}H_{22}ClNO_2$ | 125 (0.05) | C H N | 60.11 8.54 5.39 | 59.92 8.63 5.31 |
| 45 | N—(methoxymethyl)-N—(2-t-butyl-1-cyclohexen-1-yl)-2-chloroacetamide | $C_{14}H_{24}ClNO_2$ | 130 (0.05) | C H N | 61.41 8.84 5.12 | 60.60 8.82 4.86 |
| 46 | N—(methoxymethyl)-N—(6-t-butyl-1-cyclohexen-1-yl)-2-chloroacetamide | $C_{14}H_{24}ClNO_2$ | 130 (0.05) | C H N | 61.41 8.84 5.12 | 61.08 8.74 4.90 |
| 47 | N—(methoxymethyl)-N—(2-iso-propyl-6-methyl-1-cyclohexen-1-yl)-2-chloroacetamide | $C_{14}H_{24}ClNO_2$ | 140 (0.05) | C H N | 61.41 8.84 5.12 | — — — |
| 48 | N—(methoxymethyl)-N—(2-methyl-6-isopropyl-1-cyclohexen-1-yl)-2-chloroacetamide | $C_{14}H_{24}ClNO_2$ | — | C H N | 61.41 8.84 5.12 | — — — |
| 49 | N—(2-cyano-2-propoxymethyl)-N—(2,6-dimethyl-1-cyclohexen-1-yl)-2-chloroacetamide | $C_{15}H_{23}ClNO_2$ | 140 (0.05) | C H N | 60.29 7.76 9.38 | 60.29 7.76 9.37 |
| 50 | N—(cyclopropylmethoxymethyl)-N—(2,6-dimethyl-1-cyclohexen-1-yl)-2-chloroacetamide | $C_{15}H_{24}ClNO_2$ | 130 (0.05) | C H N | 63.04 8.46 4.90 | 63.02 8.50 4.91 |
| 51 | N—(sec-butoxymethyl)-N—(2,6-diethyl-1-cyclohexen-1-yl)-2-chloroacetamide | $C_{17}H_{30}ClNO_2$ | 156 (0.05) | C H N | 64.64 9.57 4.43 | 64.53 9.60 4.43 |
| 52 | N—(allyloxymethyl)-N—(2,6-diethyl-1-cyclohexen-1-yl)- | $C_{16}H_{26}ClNO_2$ | 133 (0.05) | C H | 64.09 8.74 | 63.91 8.74 |

TABLE I-continued

| Example No. | Compound | Empirical Formula | B.P. °C. (mm Hg) | Element | Analysis Calculated | Found |
|---|---|---|---|---|---|---|
| | 2-chloroacetamide | | | N | 4.67 | 4.64 |
| 53 | N—(propargyloxymethyl)-N—(2,6-diethyl-1-cyclohexen-1-yl)-2-chloroacetamide | $C_{16}H_{24}ClNO_2$ | 146 (0.05) | C H | 64.55 8.12 | 64.53 8.12 |
| | | | | N | 4.70 | 4.70 |
| 54 | N—(methoxyethoxymethyl)-N—(2,6-diethyl-1-cyclohexen-1-yl)-2-chloroacetamide | $C_{16}H_{28}ClNO_2$ | 160 (0.05) | C H | 60.46 8.88 | 60.28 8.87 |
| | | | | N | 4.41 | 4.39 |
| 55 | N—(2-methyl-2-propenoxymethyl)-N—(2,6-diethyl-1-cyclohexen-1-yl)-2-chloroacetamide | $C_{17}H_{28}ClNO_2$ | 140 (0.05) | C H | 65.06 8.99 | 64.93 9.00 |
| | | | | N | 4.46 | 4.43 |
| 56 | N—(pivaloyloxymethyl)-N—(2,6-dimethyl-1-cyclohexen-1-yl)-2-chloroacetamide | $C_{16}H_{26}ClNO_3$ | 140 (0.05) | C H | 60.85 8.30 | 60.73 8.33 |
| | | | | N | 4.43 | 4.42 |
| 57 | N—(n-propoxymethyl)-N—(2,6-diethyl-1-cyclohexen-1-yl)-2-chloracetamide | $C_{16}H_{28}ClNO_2$ | 140 (0.05) | C H | 63.66 9.35 | 63.61 9.35 |
| | | | | N | 4.64 | 4.62 |
| 58 | N—(2-methylpropoxymethyl)-N—(2,6-diethyl-1-cyclohexen-1-yl)-2-chloroacetamide | $C_{17}H_{30}ClNO_2$ | 137 (0.05) | C H | 64.64 9.57 | 64.50 9.63 |
| | | | | N | 4.43 | 4.39 |
| 59 | N—(1-methylethoxymethyl)-N—(2,6-diethyl-1-cyclohexen-1-yl)-2-chloroacetamide | $C_{16}H_{28}ClNO_2$ | 134 (0.05) | C H | 63.66 9.35 | 63.50 9.36 |
| | | | | N | 4.64 | 4.65 |
| 60 | N—(n-butoxymethyl)-N—(2,6-diethyl-1-cyclohexen-1-yl)-2-chloroacetamide | $C_{17}H_{30}ClNO_2$ | 155 (0.05) | C H | 64.64 9.57 | 64.58 9.59 |
| | | | | N | 4.43 | 4.44 |
| 61 | N—(1,1-dimethylethoxymethyl)-N—(2,6-diethyl-1-cyclohexen-1-yl)-2-chloroacetamide | $C_{17}H_{30}ClNO_2$ | 142 (0.05) | C H | 64.64 9.57 | 64.61 9.58 |
| | | | | N | 4.43 | 4.43 |
| 62 | N—(1-methylpropoxymethyl)-N—(2-methyl-1-cyclohexen-1-yl)-2-chloroacetamide | $C_{14}H_{25}ClNO_2$ | 116 (0.05) | C H | 61.41 8.84 | 61.38 8.85 |
| | | | | N | 5.12 | 5.09 |
| 63 | N—(n-propoxymethyl)-N—(2-methyl-1-cyclohexen-1-yl)-2-chloroacetamide | $C_{13}H_{22}ClNO_2$ | 119 (0.05) | C H | 60.11 8.54 | 60.23 8.62 |
| | | | | N | 5.39 | 5.37 |
| 64 | N—(1-methylethoxymethyl)-N—(2-methyl-1-cyclohexen-1-yl)-2-chloroacetamide | $C_{13}H_{22}ClNO_2$ | 107 (0.05) | C H | 60.11 8.54 | 60.02 8.58 |
| | | | | N | 5.39 | 5.35 |
| 65 | N—(2-propenoxymethyl)-N—(2-methylethyl-1-cyclohexen-1-yl)-2-chloroacetamide | $C_{15}H_{24}ClNO_2$ | 130 (0.05) | C H | 63.04 8.46 | 63.11 8.50 |
| | | | | N | 4.90 | 4.89 |
| 66 | N—(2-propenoxymethyl)-N—(2-methyl-6-ethyl-1-cyclohexen-1-yl)-2-chloroacetamide | $C_{15}H_{24}ClNO_2$ | 130 (0.05) | C H | 63.04 8.46 | 62.90 8.45 |
| | | | | N | 4.90 | 4.82 |
| 67 | N—(2-propenoxymethyl)-N—(2-methyl-1-cyclohexen-1-yl)-2-chloroacetamide | $C_{13}H_{20}ClNO_2$ | 124 (0.05) | C H | 60.58 7.82 | 60.54 7.83 |
| | | | | N | 5.43 | 5.41 |
| 68 | N—(ethoxymethyl)-N—(2-methyl-1-cyclohexen-1-yl)-2-chloroacetamide | $C_{12}H_{20}ClNO_2$ | 122 (0.05) | C H | 58.65 8.20 | 58.92 7.80 |
| | | | | N | 5.70 | 5.61 |

EXAMPLES 69–128

Yet other compounds corresponding to Formula I herein and contemplated as within the scope of this invention are shown in Table IA. In the examples, the individual compounds are those whose members are identified by Formula I.

TABLE IA

| Example No. | R | $R_1$ | $R_2$ | Y | $R_3$ | X |
|---|---|---|---|---|---|---|
| 69 | 2,6-dichloro-1-cyclohexen-1-yl | H | H | O | —$CH_3$ | Cl |
| 70 | 2,6-dichloro-1-cyclohexen-1-yl | H | H | O | -i-$C_3H_7$ | Cl |
| 71 | 2,6-dichloro-1-cyclohexen-1-yl | H | H | O | -n-$C_4H_9$ | Cl |
| 72 | 2,6-dichloro-1-cyclohexen-1-yl | H | H | O | —$CH_3$ | Br |
| 73 | 2,6-dichloro-1-cyclohexen-1-yl | H | H | O | -i-$C_3H_7$ | Br |
| 74 | 6-chloro-1-cyclohexen-1-yl | H | H | O | —$C_2H_5$ | Cl |
| 75 | " | —$CH_3$ | —$CH_3$ | O | —$CH_3$ | Cl |
| 76 | " | —$CH_3$ | —$CH_3$ | O | -n-$C_3H_7$ | Br |
| 77 | " | H | H | S | -n-$C_3H_7$ | Cl |
| 78 | " | H | H | S | -i-$C_3H_7$ | Cl |
| 79 | " | H | H | S | -i-$C_4H_9$ | Cl |
| 80 | 2-methoxy-5-methyl-1-cyclopenten-1-yl | H | H | S | -n-$C_4H_9$ | Cl |
| 81 | 2-methoxy-5-methyl-1-cyclo- | H | H | O | —$CH_3$ | Cl |

TABLE IA-continued

| Example No. | R | R₁ | R₂ | Y | R₃ | X |
|---|---|---|---|---|---|---|
| 82 | 2-ethoxy-5-ethyl-1-cyclo-penten-1-yl | —CH=CH₂ | H | O | —C₂H₅ | Cl |
| 83 | 2-isopropoxy-6-n-propyl-1-cyclohexen-1-yl | —CH₃ | —CH₃ | O | -n-C₃H₇ | Cl |
| 84 | 2-n-butoxy-6-methyl-1-cyclo-hexen-1-yl | —CH₂CH=CH₂ | H | O | —CH₃ | Cl |
| 85 | 2-methoxy-7-methyl-1-cyclo-hepten-1-yl | H | H | O | —CH₃ | Cl |
| 86 | 2-isopropoxy-7-ethyl-1-cyclo-hepten-1-yl | H | H | O | —C₂H₅ | Br |
| 87 | 2-methyl-5-methoxy-1-cyclo-penten-1-yl | phenyl | H | O | —CH₃ | Cl |
| 88 | 2-methyl-5-methoxy-1-cyclo-penten-1-yl | benzyl | H | O | —CH₃ | Cl |
| 89 | 2-ethyl-5-ethoxy-1-cyclo-penten-1-yl | —CH₃ | H | O | —C₂H₅ | Br |
| 90 | 2-ethyl-5-ethoxy-1-cyclo-penten-1-yl | —CH₃ | H | S | —C₂H₅ | Br |
| 91 | 6-n-propyl-2-isopropoxy-1-cyclohexen-1-yl | H | H | S | -n-C₃H₇ | Cl |
| 92 | 6-methyl-2-n-butoxy-1-cyclo-hexen-1-yl | H | H | O | -n-C₄H₉ | Cl |
| 93 | 2-methyl-7-methoxy-1-cyclo-hepten-1-yl | H | H | O | —CH₃ | Cl |
| 94 | 2-ethyl-7-ethoxy-1-cyclo-hepten-1-yl | —C₂H₅ | H | O | —C₂H₅ | Cl |
| 95 | 2-n-propyl-7-isopropoxy-1-cyclohepten-1-yl | —CH₃ | H | O | -n-C₃H₇ | Br |
| 96 | 2-phenyl-5-methyl-1-cyclo-penten-1-yl | H | H | O | —C₂H₅ | Cl |
| 97 | 2-phenyl-6-methyl-1-cyclo-hexen-1-yl | H | H | O | —CH₃ | Cl |
| 98 | 2-phenyl-7-methyl-1-cyclo-hepten-1-yl | H | H | O | -n-C₃H₇ | Cl |
| 99 | 2-propargyl-6-ethyl-1-cyclo-hexen-1-yl | H | H | O | -n-C₃H₇ | Cl |
| 100 | 2-vinyl-6-isopropyl-1-cyclo-hexen-1-yl | H | H | S | —CH₃ | Br |
| 101 | 2-allyl-6-isobutyl-1-cyclo-hexen-1-yl | H | H | O | —C₂H₅ | Br |
| 102 | 2-(1-naphthyl)-6-methyl-1-cyclohexen-1-yl | H | H | O | —CH₃ | Cl |
| 103 | 2,6-dimethyl-1-cyclohexen-1-yl | H | H | $\begin{array}{c}CH_3\\|\\-N-\end{array}$ | $\underset{\|}{\overset{O}{-CCH_3}}$ | Cl |
| 104 | 2,6-dimethyl-1-cyclohexen-1-yl | H | H | $\begin{array}{c}O\\\|\\C-CH_3\\\|\\-N-\end{array}$ | $\underset{\|}{\overset{O}{-CCH_3}}$ | Cl |
| 105 | 2,6-dimethyl-1-cyclohexen-1-yl | H | H | O | $\underset{\|}{\overset{O}{-CCH_3}}$ | Cl |
| 106 | 2,5-dimethyl-1-cyclo-penten-1-yl | H | H | O | $\begin{array}{c}CH_3\\\|\\-CH-CH_2OCH_3\end{array}$ | Br |
| 107 | 2,5-dimethyl-1-cyclo-penten-1-yl | H | H | O | —CH₂—CH₂O—i-C₃H₇ | Cl |
| 108 | 2,5-diethyl-1-cyclopenten-1-yl | H | —CH₃ | S | —C₂H₄OC₂H₅ | Cl |
| 109 | 2,6-dimethyl-1-cyclohexen-1-yl | H | H | O | cyclopropyl | Cl |
| 110 | 2,6-dimethyl-1-cyclohexen-1-yl | H | H | O | cyclopropyl-methyl | Cl |
| 111 | 2,6-dimethyl-1-cyclohexen-1-yl | H | H | O | phenyl | Cl |
| 112 | 2,6-dimethyl-1-cyclohexen-1-yl | H | H | O | benzyl | Cl |
| 113 | 2,6-dimethyl-1-cyclohexen-1-yl | H | H | O | 1-naphthyl | Cl |
| 114 | 2,6-dimethyl-1-cyclohexen-1-yl | propargyl | H | O | —CH₃ | Cl |
| 115 | 2,6-dimethyl-1-cyclohexen-1-yl | " | H | S | —CH₃ | Br |

TABLE IA-continued

| Example No. | R | R₁ | R₂ | Y | R₃ | X |
|---|---|---|---|---|---|---|
| 116 | 2,6-dimethyl-1-cyclohexen-1-yl | H | H | O | —CH₃ | I |
| 117 | 2,5-dimethyl-1-cyclopenten-1-yl | H | H | O | —C₂H₅ | I |
| 118 | 2-methoxyethyl-5-methyl-1-cyclopenten-1-yl | H | H | O | —CH₃ | Cl |
| 119 | 2-ethoxyethyl-5-methyl-1-cyclopenten-1-yl | H | H | O | —C₂H₅ | Cl |
| 120 | 2-n-propoxyethyl-5-methyl-1-cyclopenten-1-yl | H | H | O | -n-C₃H₇ | Br |
| 121 | 2-isobutoxyethyl-5-methyl-1-cyclopenten-1-yl | —CH₃ | —CH₃ | O | —CH₃ | Cl |
| 122 | 2-methoxyethyl-6-methyl-1-cyclohexen-1-yl | H | H | S | —CH₃ | Cl |
| 123 | 2-methoxyethyl-7-methyl-1-cyclohepten-1-yl | H | H | O | —CH₃ | Cl |
| 124 | 2,2,6-trimethyl-1-cyclohexen-1-yl | H | H | O | —C₂H₅ | Cl |
| 125 | 2,4-6-trimethyl-1-cyclohexen-1-yl | H | H | O | (CH₃)₂CH— | Cl |
| 126 | 2-propoxy-6-methyl-1-cyclohexen-1-yl | H | H | O | —C₂H₅ | Cl |
| 127 | 2-methoxy-6-methyl-1-cyclohexen-1-yl | H | H | O | (CH₃)₂CH— | Cl |
| 128 | 2-methyl-6-methoxy-1-cyclohexen-1-yl | H | H | O | CH₂=CHCH₂— | Cl |

As noted above, the compounds of this invention have been found to be effective as herbicides in the partial or total inhibition of undesirable vegetation. Tables IIA and IIIA summarize results of tests conducted to determine the pre-emergent herbicidal activity and Tables IIB and IIIB the post-emergent herbicidal activity of the compounds.

The pre-emergent test was conducted as follows:

A good grade of top soil was placed in aluminum pans and compacted to a depth of three-eighths to one-half inch from the top of the pan. On the top of the soil was placed a predetermined number of seeds or vegetative propagules of various plant species. The soil required to level fill the pans after seeding or adding vegetative propagules was weighed into a pan. A known amount of the active ingredient applied in a solvent or as a wettable powder and the soil were thoroughly mixed, and used as a cover layer for prepared pans. After treatment, the pans were moved into a greenhouse bench where they were watered from below as needed to give adequate moisture for germination and growth.

Unless noted otherwise, approximately 2 weeks after seeding and treating, the plants were observed and the results recorded. Tables IIA and IIIA below, summarize such results. The herbicidal rating was obtained by means of a fixed scale based on the percent injury of each plant species. The ratings are defined as follows:

| % Control | Rating |
|---|---|
| 0–24 | 0 |
| 25–49 | 1 |
| 50–74 | 2 |
| 75–100 | 3 |

The post-emergent tests were conducted as follows:

The active ingredients are applied in spray form to two or three week old specimens of various plant species. The spray, a solution or wettable powder suspension containing the appropriate rate of active ingredient to give the desired test rate and a surfactant, is applied to the plants. The treated plants are placed in a greenhouse and unless otherwise noted approximately two weeks later the effects ranging from no response to total inhibition are observed and recorded. The results are shown in Tables IIB and IIIB in which the post-emergent herbicidal activity index is as follows:

| % Control | Rating |
|---|---|
| 0–24 | 0 |
| 25–49 | 1 |
| 50–74 | 2 |
| 75–99 | 3 |
| 100 | 4 |

The plant species utilized in these tests are identified by letter in accordance with the following legend:

| | | |
|---|---|---|
| A Canada Thistle | E Lambsquarters | I Johnsongrass |
| B Cocklebur | F Smartweed | J Downy Brome |
| C Velvet Leaf | G Nutsedge | K Barnyardgrass |
| D Morningglory | H Quackgrass | |

TABLE IIA

| Compound of Example No. | WAT* | kg/h | \multicolumn{11}{c}{Pre-Emergent Plant Species} |
|---|---|---|---|---|---|---|---|---|---|---|---|---|---|
| | | | A | B | C | D | E | F | G | H | I | J | K |
| 1 | 2 | 11.2 | 2 | 2 | 2 | 2 | 3 | 2 | 3 | 3 | 0 | 3 | 3 |
| | 4 | 11.2 | 2 | 2 | 3 | 2 | 3 | 3 | 3 | 3 | 0 | 3 | 3 |
| | 2 | 5.6 | 1 | 1 | 1 | 2 | 3 | 1 | 2 | 3 | 0 | 2 | 3 |
| | 4 | 5.6 | 1 | 0 | 1 | 1 | 3 | 2 | 2 | 3 | 0 | 3 | 3 |

TABLE IIA-continued

| Compound of Example No. | WAT* | kg/h | Pre-Emergent Plant Species | | | | | | | | | | |
|---|---|---|---|---|---|---|---|---|---|---|---|---|---|
| | | | A | B | C | D | E | F | G | H | I | J | K |
| 10 | 2 | 11.2 | 2 | 2 | 2 | 2 | 3 | 3 | 3 | 3 | 0 | 3 | 3 |
| | 2 | 5.6 | 3 | 1 | 1 | 2 | 3 | 3 | 3 | 3 | 0 | 3 | 3 |
| 11 | 2 | 11.2 | 0 | 1 | 1 | 3 | 2 | 2 | 1 | 3 | 1 | 0 | 3 |
| | 2 | 5.6 | 0 | 0 | 1 | 2 | 2 | 1 | 1 | 1 | 0 | 0 | 3 |
| 12 | 2 | 11.2 | 3 | 2 | 1 | 2 | 3 | 3 | 3 | 3 | 1 | 3 | 3 |
| | 2 | 5.6 | 3 | 1 | 1 | 2 | 3 | 3 | 2 | 3 | 0 | 3 | 3 |
| 13 | 2 | 11.2 | 3 | 2 | 1 | 2 | 3 | 3 | 3 | 3 | 1 | 3 | 3 |
| | 2 | 5.6 | 2 | 2 | 0 | 1 | 3 | 3 | 3 | 3 | 1 | 3 | 3 |
| 14 | 2 | 11.2 | 1 | 1 | 1 | 2 | 2 | 3 | 3 | 3 | 0 | 3 | 3 |
| | 2 | 5.6 | 3 | 2 | 2 | 2 | 3 | 1 | 1 | 1 | 0 | 3 | 3 |
| 8 | 2 | 11.2 | 1 | 0 | 1 | 1 | 3 | 1 | 1 | 2 | 0 | 2 | 3 |
| | 2 | 5.6 | 0 | 1 | 1 | 1 | 2 | 1 | 0 | 0 | 0 | 0 | 3 |
| 15 | 2 | 11.2 | 3 | 2 | 3 | 2 | 3 | 3 | 3 | 3 | 2 | 3 | 3 |
| | 2 | 5.6 | 3 | 1 | 1 | 2 | 3 | 2 | 3 | 3 | 0 | 3 | 3 |
| 16 | 2 | 11.2 | 1 | 2 | 1 | 2 | 1 | 2 | 3 | 3 | 0 | 3 | 3 |
| | 2 | 5.6 | 1 | 2 | 0 | 2 | 3 | 3 | 3 | 3 | 0 | 3 | 3 |
| 17 | 2 | 11.2 | 3 | 2 | 1 | 3 | 3 | 3 | 3 | 3 | 3 | 3 | 3 |
| | 2 | 5.6 | 3 | 2 | 1 | 2 | 3 | 3 | 3 | 3 | 0 | 3 | 3 |
| 18 | 2 | 11.2 | 3 | 1 | 1 | 3 | 3 | 3 | 3 | 3 | 3 | 3 | 3 |
| | 2 | 5.6 | 3 | 1 | 1 | 2 | 3 | 3 | 3 | 3 | 1 | 3 | 3 |
| 19 | 2 | 11.2 | 1 | 1 | 3 | 2 | 3 | 3 | 3 | 3 | 1 | 3 | 3 |
| | 2 | 5.6 | 1 | 0 | 1 | 2 | 1 | 1 | 1 | 3 | 0 | 3 | 3 |
| 9 | 2 | 11.2 | 0 | 0 | 1 | 2 | 2 | 1 | 2 | 2 | 0 | 0 | 3 |
| | 2 | 5.6 | 0 | 0 | 1 | 1 | 2 | 0 | 1 | 1 | 0 | 0 | 3 |
| 20 | 2 | 11.2 | 1 | 1 | 1 | 2 | 3 | 3 | 2 | 3 | 1 | 3 | 3 |
| | 2 | 5.6 | 0 | 1 | 1 | 2 | 3 | 3 | 3 | 1 | 1 | 3 | 3 |
| 21 | 2 | 5.6 | 3 | 2 | 1 | 3 | 3 | 3 | 3 | 3 | 2 | 3 | 3 |
| 22 | 2 | 5.6 | 1 | 0 | 0 | 1 | 2 | 2 | 3 | 1 | 0 | 2 | 3 |
| 23 | 2 | 5.6 | 0 | 1 | 1 | 2 | 3 | 3 | 3 | 3 | 0 | 3 | 3 |
| 24 | 2 | 5.6 | 0 | 0 | 1 | 2 | 3 | 3 | 3 | 3 | 0 | 3 | 3 |
| 25 | 2 | 11.2 | 1 | 0 | 1 | 1 | 3 | 1 | 3 | 2 | 1 | 3 | 3 |
| | | 5.6 | 0 | 0 | 0 | 1 | 3 | 1 | 3 | 1 | 0 | 1 | 3 |
| 26 | 2 | 11.2 | 3 | 2 | 1 | 1 | 3 | 3 | 3 | 3 | 0 | 3 | 3 |
| | 2 | 5.6 | 3 | 2 | 0 | 1 | 3 | 3 | 1 | 2 | 0 | 3 | 3 |
| 27 | 2 | 11.2 | 1 | 2 | 1 | 2 | 3 | 2 | 3 | 1 | 1 | 3 | 3 |
| | 2 | 5.6 | 2 | 1 | 0 | 1 | 2 | 3 | 1 | 1 | 0 | 3 | 3 |
| 28 | 2 | 11.2 | 3 | 2 | 1 | 2 | 2 | 3 | 3 | 2 | 0 | 3 | 3 |
| | 2 | 5.5 | 0 | 1 | 1 | 1 | 3 | 3 | 0 | 2 | 0 | 1 | 3 |
| 29 | 2 | 11.2 | 2 | 1 | 1 | 1 | 3 | 2 | 3 | 3 | 1 | 3 | 3 |
| | 2 | 5.6 | 1 | 1 | 1 | 1 | 3 | 3 | 3 | 3 | 1 | 3 | 3 |
| 30 | 2 | 11.2 | 3 | 1 | 1 | 1 | 3 | 2 | 3 | 3 | 0 | 3 | 3 |
| | 2 | 5.6 | 3 | 1 | 1 | 1 | 3 | 3 | 3 | 3 | 0 | 3 | 3 |
| 31 | 2 | 11.2 | 1 | 0 | 1 | 0 | 3 | 2 | 3 | 2 | 0 | 3 | 3 |
| | 2 | 5.6 | 0 | 0 | 0 | 0 | 3 | 2 | 3 | 2 | 0 | 1 | 3 |
| 32 | 2 | 11.2 | 2 | 3 | 1 | 0 | 3 | 3 | 2 | 3 | 2 | 3 | 3 |
| | 2 | 5.6 | 2 | 1 | 0 | 0 | 3 | 2 | 1 | 3 | 0 | 3 | 3 |
| 33 | 2 | 11.2 | 0 | 1 | 0 | 0 | 1 | 1 | 2 | 1 | 0 | 3 | 3 |
| | 2 | 5.6 | 0 | 0 | 0 | 0 | 0 | 1 | 0 | 0 | 0 | 1 | 3 |
| 34 | 2 | 11.2 | 0 | 1 | 0 | 1 | 3 | 2 | 3 | 3 | 0 | 2 | 3 |
| | 2 | 5.6 | 0 | 0 | 0 | 1 | 2 | 3 | 3 | 3 | 0 | 2 | 3 |
| 35 | 2 | 11.2 | 0 | 1 | 0 | 1 | 3 | 3 | 3 | 3 | 0 | 3 | 3 |
| | 2 | 5.6 | 3 | 1 | 0 | 0 | 3 | 1 | 0 | 1 | 0 | 3 | 3 |
| 36 | 2 | 11.2 | 0 | 0 | 1 | 2 | 3 | 2 | 3 | 3 | 1 | 3 | 3 |
| | 2 | 5.6 | 0 | 0 | 0 | 2 | 2 | 1 | 3 | 1 | 0 | 3 | 3 |
| 37 | 2 | 11.2 | 0 | 1 | 1 | 2 | 3 | 3 | 3 | 3 | 1 | 3 | 3 |
| | 2 | 5.6 | 2 | 2 | 1 | 2 | 3 | 3 | 3 | 3 | 1 | 3 | 3 |
| 38 | 2 | 11.2 | 3 | 1 | 1 | 2 | 3 | 3 | 3 | 3 | 0 | 3 | 3 |
| | 2 | 5.6 | 2 | 0 | 0 | 1 | 3 | 3 | 3 | 3 | 0 | 3 | 3 |
| 39 | 2 | 11.2 | 3 | 2 | 1 | 1 | 3 | 3 | 3 | 3 | 1 | 3 | 3 |
| | 2 | 5.6 | 2 | 1 | 0 | 2 | 3 | 3 | 2 | 3 | 0 | 3 | 3 |
| 40 | 2 | 11.2 | 3 | 0 | 1 | — | 3 | 2 | 3 | 3 | 2 | 3 | 3 |
| | 2 | 5.6 | 1 | 0 | 0 | 0 | 3 | 0 | 2 | 2 | 0 | 3 | 3 |
| 41 | 2 | 11.2 | 3 | 1 | 1 | 1 | 3 | 2 | 1 | 3 | 1 | 3 | 3 |
| | 2 | 5.6 | 3 | 1 | 0 | 2 | 3 | 2 | 3 | 3 | 0 | 3 | 3 |
| 42 | 2 | 11.2 | 3 | — | 2 | 3 | 3 | 3 | 2 | 3 | 3 | 3 | 3 |
| | 2 | 5.6 | 3 | — | 2 | 3 | 3 | 2 | 2 | 3 | 2 | 3 | 3 |
| 43 | 2 | 11.2 | 1 | — | 2 | 3 | 3 | 2 | 2 | 3 | 2 | 3 | 3 |
| | 2 | 5.6 | 0 | — | 2 | 2 | 3 | 2 | 3 | 3 | 3 | 3 | 3 |
| 44 | 2 | 11.2 | 3 | 2 | 2 | 2 | 3 | 3 | 3 | 3 | 0 | 3 | 3 |
| | 2 | 5.6 | 1 | 0 | 1 | 3 | 3 | 3 | 3 | 3 | 0 | 3 | 3 |
| 45 | 2 | 11.2 | 0 | 0 | 2 | 2 | 3 | 3 | 3 | 1 | 3 | 3 | 3 |
| | 2 | 5.6 | 0 | 0 | 2 | 2 | 3 | 3 | 3 | 2 | 3 | 3 | 3 |
| 46 | 2 | 11.2 | 3 | 0 | 2 | 1 | 3 | 3 | 3 | 1 | 0 | 3 | 3 |
| | 2 | 5.6 | 0 | 0 | 1 | 0 | 3 | 0 | 3 | 1 | 0 | 3 | 3 |
| 49 | 2 | 11.2 | 2 | 1 | 2 | 3 | 3 | 3 | 3 | 3 | 0 | 3 | 3 |
| | 2 | 5.6 | 1 | 2 | 1 | 3 | 3 | 2 | 1 | 3 | 0 | 3 | 3 |
| 50 | 2 | 11.2 | 3 | 3 | 2 | 3 | 3 | 3 | 2 | 3 | 1 | 3 | 3 |
| | 2 | 5.6 | 3 | 2 | 2 | 3 | 3 | 3 | 3 | 3 | 3 | 3 | 3 |

TABLE IIA-continued

Pre-Emergent

| Compound of Example No. | WAT* | kg/h | A | B | C | D | E | F | G | H | I | J | K |
|---|---|---|---|---|---|---|---|---|---|---|---|---|---|
| 51 | 2 | 11.2 | 1 | 2 | 3 | 2 | 3 | 2 | 3 | 3 | 1 | 3 | 3 |
|  | 2 | 5.6 | 2 | 1 | 0 | 2 | 3 | 3 | 3 | 3 | 2 | 3 | 3 |
| 52 | 2 | 11.2 | 1 | 1 | 0 | 1 | 3 | 2 | 3 | 3 | 1 | 3 | 3 |
|  | 2 | 5.6 | 1 | 1 | 0 | — | 3 | 3 | 3 | 2 | 1 | 3 | 3 |
| 53 | 2 | 11.2 | 3 | 2 | 0 | — | 3 | 3 | 3 | 2 | 0 | 3 | 3 |
|  | 2 | 5.6 | 0 | 0 | 0 | 1 | 3 | 1 | 1 | 1 | 0 | 3 | 3 |
| 54 | 2 | 11.2 | 2 | 1 | 1 | 2 | 3 | 3 | 3 | 2 | 2 | 3 | 3 |
|  | 2 | 5.6 | 1 | 0 | 0 | — | 3 | 3 | 2 | 3 | 2 | 3 | 3 |
| 55 | 2 | 11.2 | 0 | 1 | 0 | 1 | 3 | 3 | 3 | 1 | 0 | 3 | 3 |
|  | 2 | 5.6 | 0 | — | 0 | — | 3 | 3 | 0 | 0 | 0 | 3 | 3 |
| 56 | 2 | 11.2 | 3 | — | 2 | — | 3 | 1 | 2 | 0 | 0 | 3 | 3 |
|  | 2 | 5.6 | 0 | — | 1 | — | 3 | 0 | 1 | 1 | 0 | 1 | 3 |
| 2 | 2 | 11.2 | 3 | 3 | 3 | 3 | 3 | 3 | 3 | 3 | 1 | 3 | 3 |
|  | 2 | 5.6 | 3 | 3 | 3 | 3 | 3 | 3 | 1 | 3 | 0 | 3 | 3 |
| 3 | 2 | 11.2 | 3 | 3 | 2 | 3 | 3 | 3 | 3 | 3 | 1 | 3 | 3 |
|  | 2 | 5.6 | 3 | 0 | 1 | 2 | 3 | 3 | 3 | 3 | 0 | 3 | 3 |
| 4 | 2 | 11.2 | 3 | 0 | 3 | 2 | 3 | 3 | 3 | 3 | 1 | 3 | 3 |
|  | 2 | 5.6 | 3 | — | 1 | 3 | 3 | 3 | 3 | 3 | 1 | 3 | 3 |
| 5 | 2 | 11.2 | 3 | — | 1 | 3 | 3 | 3 | 3 | 3 | 3 | 3 | 3 |
|  |  | 5.6 | 3 | — | 1 | 2 | 3 | 3 | 3 | 3 | 3 | 3 | 3 |
| 65 | 2 | 11.2 | 3 | 1 | 1 | 2 | 3 | 3 | 3 | 3 | 0 | 3 | 3 |
|  |  | 5.6 | 0 | 0 | 0 | 0 | 2 | 2 | 3 | 3 | 0 | 3 | 3 |
| 66 | 2 | 11.2 | 3 | 2 | 1 | 2 | 3 | 3 | 3 | 3 | 3 | 3 | 3 |
|  |  | 5.6 | 2 | 1 | 1 | 3 | 3 | 3 | 3 | 3 | 0 | 3 | 3 |
| 67 | 2 | 11.2 | 3 | 3 | 3 | 3 | 3 | 3 | 3 | 3 | 0 | 3 | 3 |
|  |  | 5.6 | 2 | 1 | 1 | 3 | 3 | 3 | 3 | 3 | 0 | 3 | 3 |
| 47 | 2 | 11.2 | 1 | 2 | 2 | 3 | 3 | 3 | 3 | 3 | 0 | 3 | 3 |
|  | 2 | 5.6 | 2 | 0 | 1 | 2 | 3 | 0 | 3 | 3 | 0 | 3 | 3 |

*Weeks after treatment

TABLE IIB

Post-Emergent

| Compound of Example No. | WAT* | kg/h | A | B | C | D | E | F | G | H | I | J | K |
|---|---|---|---|---|---|---|---|---|---|---|---|---|---|
| 1 | 2 | 11.2 | 0 | 0 | 0 | 1 | 0 | 0 | 1 | 0 | 0 | 0 | 1 |
| 10 | 2 | 11.2 | 1 | 1 | 0 | 2 | 1 | 0 | 0 | 0 | 0 | 0 | 1 |
| 11 | 2 | 11.2 | 0 | 1 | 1 | 1 | 3 | 0 | 1 | 0 | 0 | 0 | 2 |
| 12 | 2 | 11.2 | 0 | 1 | 1 | 2 | 1 | 1 | 1 | 0 | 1 | 0 | 2 |
| 13 | 2 | 11.2 | 0 | 2 | 0 | 2 | 3 | 1 | 1 | 0 | 1 | 0 | 2 |
| 14 | 2 | 11.2 | 0 | 1 | 0 | 1 | 1 | 0 | 0 | 0 | 0 | 0 | 1 |
| 8 | 2 | 11.2 | 0 | 1 | 0 | 2 | 2 | 1 | 0 | 0 | 0 | 0 | 2 |
| 15 | 2 | 11.2 | 1 | 1 | 0 | 2 | 3 | 1 | 2 | 0 | 0 | 0 | 2 |
| 16 | 2 | 11.2 | 0 | 1 | 0 | 1 | 1 | 1 | 0 | 0 | 0 | 0 | 1 |
| 17 | 2 | 11.2 | 0 | — | 0 | 2 | 0 | 1 | 0 | 0 | 0 | 0 | 1 |
| 18 | 2 | 11.2 | 1 | 0 | 1 | 1 | 0 | 1 | 1 | 0 | 0 | 0 | 2 |
| 19 | 2 | 11.2 | — | 1 | 1 | 2 | — | 2 | 1 | 1 | 0 | 0 | 2 |
| 9 | 2 | 11.2 | 0 | — | 0 | 1 | 2 | 2 | 0 | 0 | 0 | 0 | 1 |
| 20 | 2 | 11.2 | 0 | 1 | 0 | 1 | 3 | 3 | 2 | 1 | 0 | 0 | 2 |
| 21 | 2 | 11.2 | 0 | 1 | 1 | 1 | 1 | 1 | 1 | 0 | 0 | 1 | 1 |
| 22 | 2 | 11.2 | — | 0 | 0 | 0 | 0 | 1 | 0 | 0 | 0 | 0 | 1 |
| 23 | 2 | 11.2 | — | 0 | 0 | 1 | 1 | 1 | 0 | 0 | 0 | 0 | 0 |
| 24 | 2 | 11.2 | 0 | 1 | 1 | 1 | 0 | 0 | 2 | 0 | 0 | 0 | 2 |
| 25 | 2 | 11.2 | 0 | 2 | 0 | 0 | 0 | 0 | 1 | 0 | 0 | 0 | 2 |
| 26 | 2 | 11.2 | 0 | 1 | 0 | 1 | 0 | 0 | 0 | 0 | 0 | 0 | 1 |
| 27 | 2 | 11.2 | 0 | 1 | 0 | 1 | 0 | 0 | 0 | 0 | 0 | 0 | 1 |
| 28 | 2 | 11.2 | 0 | 1 | 0 | 1 | 1 | 2 | 0 | 0 | 0 | 0 | 1 |
| 29 | 2 | 11.2 | 0 | 0 | 0 | 1 | 0 | 0 | 1 | 0 | 0 | 0 | 1 |
| 30 | 2 | 11.2 | 0 | 0 | 0 | 1 | 0 | 2 | 1 | 0 | 0 | 0 | 1 |
| 31 | 2 | 11.2 | 0 | 1 | 0 | 1 | 2 | 1 | 1 | 0 | 0 | 0 | 1 |
| 32 | 2 | 11.2 | 0 | 1 | 1 | 1 | — | 2 | 0 | 0 | 0 | 0 | 2 |
| 35 | 2 | 11.2 | 0 | 0 | 0 | 0 | 0 | 1 | 1 | 0 | 0 | 0 | 2 |
| 37 | 2 | 11.2 | 0 | 0 | 0 | 0 | 0 | 3 | 1 | 0 | 0 | 0 | 2 |
| 38 | 2 | 11.2 | — | 0 | 0 | 0 | 0 | 2 | 2 | 0 | 0 | 2 | 0 |
| 39 | 2 | 11.2 | 0 | 1 | 0 | 0 | 3 | 1 | 1 | 0 | 0 | 0 | 1 |
| 40 | 2 | 11.2 | 0 | 1 | 0 | 1 | 0 | 0 | 0 | 0 | 0 | 0 | 2 |
| 41 | 2 | 11.2 | 0 | 0 | 0 | 1 | 0 | 0 | 0 | 0 | 0 | 0 | 1 |
| 42 | 2 | 11.2 | 0 | 1 | 0 | 1 | 0 | 1 | 1 | 0 | 0 | 0 | 1 |
| 43 | 2 | 11.2 | 0 | 1 | 0 | 1 | 1 | 1 | 1 | 0 | 0 | 0 | 3 |
| 44 | 2 | 11.2 | — | 2 | 0 | 2 | 2 | 3 | 1 | 0 | 0 | 1 | 3 |
| 45 | 2 | 11.2 | — | 1 | 0 | 1 | 1 | 1 | 1 | 0 | 1 | 0 | 2 |
| 46 | 2 | 11.2 | — | 1 | 0 | 1 | 0 | 2 | 0 | 0 | — | 0 | 2 |
| 50 | 2 | 11.2 | 0 | 1 | 0 | 1 | 1 | 2 | 0 | 0 | 0 | 0 | 2 |
| 51 | 2 | 11.2 | 0 | 0 | 0 | 1 | 0 | 1 | 1 | 0 | 0 | 0 | 2 |
| 52 | 2 | 11.2 | 0 | 2 | 1 | 2 | 0 | 3 | 1 | 0 | 0 | 0 | 2 |
| 53 | 2 | 11.2 | 0 | 1 | 0 | 1 | 0 | 2 | 0 | 0 | 0 | 0 | 2 |

TABLE IIB-continued

| Compound of Example No. | WAT* | kg/h | Post-Emergent Plant Species | | | | | | | | | | |
|---|---|---|---|---|---|---|---|---|---|---|---|---|---|
| | | | A | B | C | D | E | F | G | H | I | J | K |
| 54 | 2 | 11.2 | — | 1 | 0 | 1 | 0 | 2 | 1 | 0 | 0 | 0 | 3 |
| 55 | 2 | 11.2 | 0 | 1 | 1 | 1 | 0 | 0 | 2 | 0 | 0 | 0 | 3 |
| 2 | 2 | 11.2 | 0 | 2 | 1 | 1 | 1 | 1 | 2 | 0 | 0 | 1 | 3 |
| 3 | 2 | 11.2 | 1 | 2 | 0 | 1 | 3 | 2 | 2 | 0 | 0 | 1 | 3 |
| 4 | 2 | 11.2 | 1 | 2 | 0 | 2 | 3 | 2 | 2 | 0 | 0 | 0 | 3 |
| 5 | 2 | 11.2 | 0 | 2 | 0 | 2 | 1 | 4 | 2 | 1 | 1 | 0 | 3 |
| 65 | 2 | 11.2 | 1 | 1 | 0 | 1 | 1 | 1 | 1 | 1 | 0 | 0 | 2 |
| 66 | 2 | 11.2 | 2 | 2 | 2 | 3 | 4 | 2 | 2 | 1 | 0 | 2 | 3 |
| 67 | 2 | 11.2 | 0 | 1 | 0 | 1 | 1 | 3 | 1 | 0 | 0 | 0 | 2 |
| 47 | 2 | 11.2 | 0 | 2 | 0 | 1 | 1 | 2 | 0 | 0 | 0 | 1 | 3 |

*Weeks after treatment

The compounds were further tested by utilizing the above procedure on the following plant species:

| L | Soybean | R | Hemp Sesbania |
|---|---|---|---|
| M | Sugarbeet | E | Lambsquarters |
| N | Wheat | F | Smartweed |
| O | Rice | C | Velvet Leaf |
| P | Sorghum | J | *Bromus tectorum* (Downy brome) |
| B | Cocklebur | S | Panicum Spp. |
| Q | Wild Buckwheat | K | Barnyardgrass |
| D | Morningglory | T | Crabgrass |

The results are summarized in Tables IIIA and IIIB.

TABLE IIIA

| Compound of Ex. No. | WAT* | kg/h | Pre-Emergent Plant Species | | | | | | | | | | | | | | |
|---|---|---|---|---|---|---|---|---|---|---|---|---|---|---|---|---|---|
| | | | L | M | N | O | P | B | Q | D | R | E | F | C | J | S | K | T |
| 1 | 2 | 5.6 | 2 | 3 | 2 | 3 | 3 | 1 | 1 | 1 | 3 | 2 | 2 | 3 | 3 | 3 | 3 |
| | 2 | 1.12 | 1 | 2 | 1 | 3 | 3 | 1 | 0 | 1 | 0 | 2 | 2 | 0 | 3 | 3 | 3 | 3 |
| | 2 | 0.28 | 0 | 1 | 1 | 1 | 1 | 0 | 0 | 1 | 0 | 1 | 1 | 0 | 2 | 3 | 3 | 3 |
| | 2 | 0.06 | 0 | 0 | 0 | 1 | 0 | 0 | 0 | 1 | 0 | 1 | 0 | 0 | 0 | 2 | 3 | 3 |
| | 2 | 0.01 | 0 | 0 | 0 | 0 | 0 | 0 | 0 | 0 | 0 | 0 | 0 | 0 | | 1 | 1 |
| 10 | 2 | 5.6 | 3 | 3 | 3 | 3 | 3 | 1 | 2 | 3 | 3 | 3 | 3 | 3 | 3 | 3 | 3 | 3 |
| | 2 | 1.12 | 2 | 2 | 3 | 3 | 3 | 1 | 2 | 2 | 3 | 3 | 3 | 1 | 3 | 3 | 3 | 3 |
| | 2 | 0.28 | 1 | 3 | 2 | 3 | 3 | 0 | 2 | 1 | 3 | 3 | 3 | 0 | 3 | 3 | 3 | 3 |
| | 2 | 0.06 | 1 | 1 | 1 | 2 | 2 | 0 | 1 | 1 | 2 | 2 | 2 | 0 | 1 | 3 | 3 | 3 |
| | 2 | 0.01 | 0 | 1 | 0 | 0 | 0 | 0 | 0 | 0 | 1 | 0 | 0 | 0 | 0 | 2 | 3 | 2 |
| 11 | 2 | 5.6 | 1 | 2 | 2 | 3 | 3 | 2 | 3 | 3 | 2 | 2 | 2 | 2 | 3 | 3 | 3 | 3 |
| | 2 | 1.12 | 0 | 1 | 1 | 3 | 1 | 2 | 1 | 1 | 1 | 1 | 1 | 1 | 1 | 3 | 3 | 3 |
| | 2 | 0.28 | 0 | 0 | 0 | 0 | 0 | 0 | 1 | 0 | 0 | 0 | 0 | 1 | 0 | 3 | 3 | 3 |
| 12 | 2 | 5.6 | 2 | 2 | 3 | 3 | 3 | 1 | 1 | 3 | 2 | 3 | 3 | 1 | 3 | 3 | 3 | 3 |
| | 2 | 1.12 | 1 | 2 | 3 | 3 | 3 | 0 | 3 | 2 | 3 | 3 | 3 | 0 | 3 | 3 | 3 | 3 |
| | 2 | 0.28 | 0 | 1 | 1 | 2 | 3 | 0 | 0 | 1 | 1 | 3 | 2 | 0 | 2 | 3 | 3 | 3 |
| | 2 | 0.06 | 0 | 0 | 0 | 1 | 1 | 0 | 0 | 1 | 0 | 0 | 1 | 0 | 1 | 3 | 3 | 3 |
| | 2 | 0.01 | 0 | 0 | 0 | 0 | 0 | 0 | 0 | 0 | 0 | 0 | 0 | 0 | 1 | 1 | 3 | 2 |
| 13 | 2 | 5.6 | 2 | 2 | 3 | 3 | 3 | 3 | 3 | 3 | 2 | 3 | 3 | 1 | 3 | 3 | 3 | 3 |
| | 2 | 1.12 | 1 | 2 | 3 | 3 | 3 | 0 | 3 | 2 | 2 | 3 | 3 | 0 | 3 | 3 | 3 | 3 |
| | 2 | 0.28 | 1 | 1 | 1 | 2 | 3 | 1 | 3 | 1 | 1 | 3 | 3 | 0 | 2 | 3 | 3 | 3 |
| | 2 | 0.06 | 1 | 1 | 0 | 1 | 3 | 1 | 3 | 0 | 1 | 3 | 3 | 0 | 1 | 3 | 3 | 3 |
| | 2 | 0.01 | 1 | — | 0 | 1 | 0 | 0 | 3 | 0 | 1 | 1 | 2 | 0 | 0 | 3 | 3 | 2 |
| 14 | 2 | 5.6 | 0 | 3 | 2 | 3 | 3 | 0 | 1 | 2 | 2 | 3 | 3 | 0 | 3 | 3 | 3 | 3 |
| | 2 | 1.12 | 0 | 1 | 1 | 2 | 3 | 0 | 0 | 0 | 1 | 2 | 2 | 0 | 2 | 3 | 3 | 3 |
| | 2 | 0.28 | 0 | 0 | 0 | 1 | 2 | 0 | 0 | 0 | 1 | 1 | 2 | 0 | 0 | 3 | 3 | 3 |
| | 2 | 0.06 | 0 | 0 | 0 | 0 | 0 | 0 | 0 | 0 | 0 | 1 | 2 | 0 | 0 | 1 | 2 | 3 |
| 8 | 2 | 5.6 | 0 | 2 | 3 | 3 | 3 | 0 | 1 | 1 | 2 | 3 | 3 | 1 | 3 | 3 | 3 | 3 |
| | 2 | 1.12 | 0 | 0 | 0 | 1 | 0 | 0 | 1 | 0 | 0 | 3 | 1 | 0 | 0 | 3 | 3 | 3 |
| | 2 | 0.28 | 0 | 0 | 0 | 0 | 0 | 0 | 0 | 0 | 0 | 1 | 1 | 0 | 0 | 3 | 3 | 1 |
| 15 | 2 | 5.6 | 3 | 3 | 3 | 3 | 3 | 3 | 3 | 3 | 3 | 3 | 3 | 3 | 3 | 3 | 3 | 3 |
| | 2 | 1.12 | 2 | 2 | 3 | 3 | 3 | 2 | 2 | 2 | 3 | 3 | 3 | 1 | 3 | 3 | 3 | 3 |
| | 2 | 0.28 | 0 | 2 | 1 | 2 | 3 | 1 | 3 | 0 | 1 | 3 | 3 | 0 | 3 | 3 | 3 | 3 |
| | 2 | 0.06 | 0 | 1 | 1 | 1 | 1 | 0 | 1 | 0 | 1 | 2 | 3 | 0 | 1 | 3 | 3 | 3 |
| | 2 | 0.01 | 0 | 1 | 0 | 0 | 0 | 0 | 0 | 0 | 1 | 1 | 2 | 0 | 1 | 3 | 3 | 3 |
| 16 | 2 | 5.6 | 0 | 2 | 1 | 3 | 3 | 0 | 1 | 2 | 2 | 3 | 2 | 0 | 2 | 3 | 3 | 3 |
| | 2 | 1.12 | 0 | 2 | 1 | 1 | 2 | 0 | 0 | 1 | 1 | 2 | 1 | 0 | 1 | 3 | 3 | 3 |
| | 2 | 0.28 | 0 | 1 | 0 | 1 | 0 | 0 | 0 | 0 | 1 | 1 | 0 | 0 | 0 | 3 | 3 | 3 |
| | 2 | 0.06 | 0 | 1 | 0 | 0 | 0 | 1 | 0 | 1 | 1 | 1 | 1 | 0 | 0 | 2 | 3 | 3 |
| 17 | 2 | 5.6 | 2 | 3 | 3 | 3 | 3 | 1 | 2 | 2 | 3 | 3 | 3 | 1 | 3 | 3 | 3 | 3 |
| | 2 | 1.12 | 1 | 2 | 3 | 3 | 3 | 0 | 1 | 2 | 2 | 3 | 3 | 1 | 3 | 3 | 3 | 3 |
| | 2 | 0.28 | 0 | 2 | 0 | 3 | 3 | 0 | 0 | 0 | 2 | 3 | 3 | 0 | 2 | 3 | 3 | 3 |
| | 2 | 0.06 | 0 | 0 | 0 | 1 | 1 | 0 | 0 | 1 | 0 | 1 | 0 | 1 | 3 | 3 | 3 |
| | 2 | 0.01 | 0 | 0 | 0 | 0 | 0 | 0 | 0 | 0 | 0 | 0 | 0 | 0 | 0 | 3 | 1 |
| 18 | 2 | 5.6 | 3 | 3 | 3 | 3 | 3 | 1 | 2 | 3 | 2 | 3 | 3 | 1 | 3 | 3 | 3 | 3 |
| | 2 | 1.12 | 1 | 3 | 2 | 3 | 3 | 0 | 1 | 2 | 2 | 3 | 3 | 0 | 3 | 3 | 3 | 3 |
| | 2 | 0.28 | 0 | 3 | 1 | 3 | 3 | 1 | 1 | 1 | 2 | 2 | 2 | 0 | 3 | 3 | 3 | 3 |
| | 2 | 0.06 | 0 | 0 | 0 | 1 | 1 | 0 | 0 | 1 | 0 | 1 | 0 | 1 | 3 | 3 | 3 |
| | 2 | 0.01 | 0 | 0 | 0 | 0 | 0 | 0 | 0 | 0 | 0 | 0 | 0 | 0 | 1 | 3 | 3 |

TABLE IIIA-continued

| | | | Pre-Emergent Plant Species | | | | | | | | | | | | | | | |
|---|---|---|---|---|---|---|---|---|---|---|---|---|---|---|---|---|---|---|
| Compound of Ex. No. | WAT* | kg/h | L | M | N | O | P | B | Q | D | R | E | F | C | J | S | K | T |
| 19 | 2 | 5.6 | 3 | 3 | 3 | 3 | 3 | 1 | 1 | 2 | 2 | 3 | 3 | 1 | 3 | 3 | 3 | 3 |
| | 2 | 1.12 | 0 | 1 | 1 | 1 | 1 | 0 | 0 | 0 | 0 | 1 | 2 | 0 | 1 | 1 | 3 | 3 |
| | 2 | 0.28 | 0 | 0 | 0 | 0 | 1 | 0 | 0 | 0 | 0 | 1 | 1 | 0 | 0 | 1 | 2 | 2 |
| | 2 | 0.06 | 0 | 0 | 0 | 0 | 0 | 0 | 0 | 0 | 0 | 0 | 0 | 0 | 0 | 0 | 1 | 2 |
| 9 | 2 | 5.6 | 0 | 3 | 1 | 0 | 2 | 1 | 1 | 0 | 1 | 1 | 1 | 0 | 1 | 3 | 3 | 3 |
| | 2 | 1.12 | 0 | 1 | 0 | 0 | 0 | 0 | 0 | 0 | 1 | 1 | 1 | 0 | 0 | | 2 | 3 |
| | 2 | 0.28 | 0 | — | 0 | 0 | 0 | 0 | — | 0 | 0 | 0 | 0 | 0 | 0 | — | 2 | 3 |
| 20 | 2 | 5.6 | 2 | 3 | 3 | 3 | 3 | 1 | 1 | 2 | 2 | 3 | 3 | 1 | 3 | 3 | 3 | 3 |
| | 2 | 1.12 | 0 | 2 | 2 | 2 | 3 | 1 | 1 | 1 | 2 | 3 | 3 | 0 | 2 | 3 | 3 | 3 |
| | 2 | 0.28 | 0 | 1 | 0 | 1 | 1 | 0 | 0 | 0 | 1 | 1 | 2 | 0 | 1 | 3 | 3 | 3 |
| | 2 | 0.06 | 0 | 1 | 0 | 0 | 0 | 0 | 0 | 0 | 0 | 1 | 0 | 0 | 3 | 3 | 3 | |
| 21 | 2 | 5.6 | 1 | 2 | 3 | 3 | 3 | 0 | 1 | 2 | 1 | 3 | 3 | 0 | 3 | 3 | 3 | 3 |
| | 2 | 1.12 | 2 | 1 | 2 | 3 | 3 | 0 | 0 | 1 | 1 | 3 | 2 | 0 | 3 | 3 | 3 | 3 |
| | 2 | 0.28 | 2 | 1 | 2 | 2 | 3 | 0 | 0 | 0 | 1 | 0 | 3 | 0 | 2 | 3 | 3 | 3 |
| | 2 | 0.06 | 0 | 0 | 0 | 0 | 1 | 0 | 0 | 0 | 0 | 0 | 0 | 0 | 1 | 3 | 3 | 3 |
| | 2 | 0.01 | 0 | 0 | 0 | 0 | 0 | 0 | 0 | 0 | 0 | 0 | 0 | 0 | 0 | 2 | 3 | 2 |
| 22 | 2 | 5.6 | 1 | 3 | 3 | 3 | 3 | 1 | 2 | 2 | 2 | 3 | 3 | 0 | 3 | 3 | 3 | 3 |
| | 2 | 1.12 | 0 | 2 | 1 | 2 | 3 | 0 | 2 | 1 | 2 | 2 | 3 | 0 | 3 | 3 | 3 | 3 |
| | 2 | 0.28 | 0 | 1 | 0 | 0 | 0 | 0 | 0 | 0 | 1 | 2 | 2 | 0 | 1 | 3 | 3 | 3 |
| | 2 | 0.06 | 0 | 1 | 0 | 0 | 0 | 0 | 0 | 0 | 0 | 0 | 1 | 0 | 0 | 3 | 3 | 3 |
| | 2 | 0.01 | 0 | 0 | 0 | 0 | 0 | 0 | 1 | 0 | 0 | 0 | 0 | 2 | 0 | 0 | 1 | 1 |
| 23 | 2 | 5.6 | 1 | 2 | 3 | 3 | 3 | 0 | 2 | 2 | 2 | 3 | 3 | 1 | 3 | 3 | 3 | 3 |
| | 2 | 1.12 | 0 | 0 | 1 | 1 | 3 | 0 | 0 | 0 | 0 | 2 | 3 | 0 | 0 | 3 | 3 | 3 |
| | 2 | 0.28 | 0 | 0 | 1 | 0 | 3 | 0 | 0 | 0 | 0 | 0 | 2 | 0 | 1 | 3 | 3 | 3 |
| | 2 | 0.06 | 0 | 1 | 0 | 0 | 1 | 0 | 0 | 0 | 0 | 0 | 0 | 0 | 0 | 3 | 3 | 3 |
| | 2 | 0.01 | 0 | 0 | 0 | 0 | 0 | 0 | 0 | 0 | 0 | 0 | 0 | 0 | 0 | 0 | 2 | 3 |
| 24 | 2 | 5.6 | 3 | 3 | 3 | 3 | 3 | 0 | 1 | 2 | 2 | 3 | 3 | 0 | 3 | 3 | 3 | 3 |
| | 2 | 1.12 | 0 | 1 | 1 | 3 | 2 | 0 | 0 | 0 | 1 | 0 | 2 | 0 | 1 | 3 | 3 | 3 |
| | 2 | 0.28 | 0 | — | 0 | 1 | 2 | 0 | 2 | 0 | 0 | 0 | 2 | 0 | 0 | 3 | 3 | 3 |
| | 2 | 0.06 | 0 | 0 | 1 | 0 | 0 | 0 | 0 | 0 | 0 | 0 | 0 | 0 | 0 | 2 | 3 | 3 |
| 25 | 2 | 5.6 | 2 | 1 | 2 | 3 | 3 | 0 | 1 | 1 | 2 | 3 | 2 | 1 | 3 | 3 | 3 | 3 |
| | 2 | 1.12 | 0 | 1 | 0 | 1 | 1 | 0 | 0 | 0 | 1 | 1 | 2 | 0 | 0 | 3 | 3 | 3 |
| | 2 | 0.28 | 0 | 0 | 0 | 0 | 0 | 0 | 0 | 0 | 0 | 0 | 0 | 0 | 0 | 3 | 3 | 3 |
| | 2 | 0.06 | 0 | 0 | 0 | 0 | 0 | 0 | 0 | 0 | 0 | 3 | 0 | 1 | 0 | 1 | 2 | |
| 26 | 2 | 5.6 | 0 | 1 | 3 | 3 | 3 | 1 | 2 | 1 | 2 | 3 | 3 | 0 | 3 | 3 | 3 | 3 |
| | 2 | 1.12 | 0 | 1 | 1 | 2 | 3 | 0 | 1 | 0 | 0 | 1 | 3 | 0 | 1 | 3 | 3 | 3 |
| | 2 | 0.28 | 0 | 0 | 1 | 1 | 2 | 0 | 0 | 0 | 0 | 0 | 2 | 0 | 2 | 3 | 3 | 3 |
| | 2 | 0.06 | 0 | 1 | 0 | 1 | 1 | 0 | 0 | 0 | — | 0 | 2 | 0 | 3 | 3 | 3 | |
| | 2 | 0.01 | 0 | 0 | 0 | 0 | 0 | 0 | 0 | 0 | 0 | 0 | 0 | 0 | 0 | 1 | 1 | |
| 27 | 2 | 5.6 | 2 | 3 | 3 | 3 | 3 | 0 | 1 | 1 | 3 | 3 | 3 | 2 | 3 | 3 | 3 | 3 |
| | 2 | 1.12 | 0 | 1 | 3 | 3 | 3 | 0 | 0 | 0 | 3 | 3 | 3 | 1 | 3 | 3 | 3 | 3 |
| | 2 | 0.28 | 0 | 2 | 2 | 3 | 3 | 0 | 0 | 0 | 1 | 3 | 2 | 0 | 3 | 3 | 3 | 3 |
| | 2 | 0.06 | 0 | 1 | 1 | 2 | 2 | 0 | — | 0 | 0 | 1 | 1 | 0 | 1 | 3 | 3 | 3 |
| | 2 | 0.01 | 0 | 0 | 0 | 0 | 0 | 0 | 0 | 0 | 0 | 0 | 0 | 0 | 0 | 0 | 1 | 0 |
| 28 | 2 | 5.6 | 2 | 3 | 3 | 3 | 3 | 1 | 1 | 1 | 2 | 3 | 3 | 2 | 3 | 3 | 3 | 3 |
| | 2 | 1.12 | 0 | 1 | 3 | 2 | 3 | 0 | 0 | 0 | 1 | 3 | 3 | 0 | 2 | 3 | 3 | 3 |
| | 2 | 0.28 | 0 | 0 | 2 | 2 | 3 | 0 | 0 | 0 | 1 | 0 | 2 | 0 | 3 | 3 | 3 | 3 |
| | 2 | 0.06 | 0 | 0 | 0 | 1 | 2 | 0 | 0 | 0 | 0 | 0 | 0 | 0 | 0 | 3 | 3 | 3 |
| | 2 | 0.01 | 0 | 0 | 0 | 0 | 0 | 0 | 0 | 0 | 0 | 0 | 0 | 0 | 0 | 0 | 2 | 2 |
| 29 | 2 | 5.6 | 1 | 3 | 3 | 3 | 3 | 1 | 2 | 1 | 1 | 3 | 3 | 0 | 3 | 3 | 3 | 3 |
| | 2 | 1.12 | 0 | 1 | 1 | 1 | 3 | 0 | 1 | 0 | 0 | 2 | 3 | 0 | 3 | 3 | 3 | 3 |
| | 2 | 0.28 | 0 | 0 | 0 | 1 | 2 | 0 | 0 | 0 | 0 | 0 | 0 | 0 | 0 | 3 | 3 | 3 |
| | 2 | 0.06 | 0 | 0 | 0 | 0 | 0 | 0 | 0 | 0 | 0 | 0 | 0 | 0 | 0 | 2 | 3 | 2 |
| | 2 | 0.01 | 0 | 0 | 0 | 0 | 0 | 0 | 0 | 0 | 0 | 0 | 0 | 0 | 0 | 0 | 3 | 0 |
| 30 | 2 | 5.6 | 3 | 2 | 3 | 3 | 3 | 2 | 2 | 2 | 2 | 2 | 3 | 3 | 2 | 3 | 3 | 3 |
| | 2 | 1.12 | 1 | 1 | 2 | 2 | 3 | 1 | 1 | 1 | 1 | 3 | 3 | 2 | 1 | 3 | 3 | 3 |
| | 2 | 0.28 | 0 | 1 | 1 | 1 | 3 | 3 | 0 | 0 | 1 | 3 | 3 | 1 | 1 | 2 | 3 | 3 |
| | 2 | 0.06 | 0 | 0 | 0 | 0 | 2 | 0 | 0 | 0 | 0 | 1 | 1 | 3 | 1 | 3 | 3 | |
| | 2 | 0.01 | 0 | 0 | 0 | 0 | 0 | 0 | 0 | 0 | 0 | 0 | 0 | 1 | 1 | 1 | 2 | |
| 31 | 2 | 5.6 | 0 | 1 | 1 | 3 | 3 | 0 | 0 | 0 | 0 | 3 | 1 | 1 | 3 | 3 | 3 | 3 |
| | 2 | 1.12 | 0 | 0 | 1 | 1 | 2 | 0 | 1 | 0 | 0 | 1 | 1 | 0 | 0 | 3 | 3 | 3 |
| | 2 | 0.28 | 0 | 0 | 0 | 0 | 0 | 0 | 0 | 0 | 0 | 0 | 0 | 0 | 0 | 1 | 3 | 2 |
| | 2 | 0.06 | 0 | 0 | 0 | 0 | 0 | 0 | 0 | 0 | 0 | 0 | 0 | 0 | 0 | 3 | 0 | |
| 32 | 2 | 5.6 | 1 | 1 | 3 | 3 | 3 | 1 | 3 | 0 | 2 | — | 3 | 0 | 3 | 3 | 3 | 3 |
| | 2 | 1.12 | 0 | — | 2 | 2 | 3 | 0 | 3 | 0 | 0 | — | 3 | 0 | 3 | 3 | 3 | |
| | 2 | 0.28 | 0 | 1 | 1 | 1 | 2 | 0 | 3 | 0 | 0 | — | 3 | 0 | 2 | 3 | 3 | 3 |
| 33 | 2 | 5.6 | 0 | 0 | 1 | 1 | 2 | 0 | 1 | 0 | 0 | — | 3 | 0 | 2 | 3 | 3 | 3 |
| | 2 | 1.12 | 0 | 0 | 0 | 0 | 0 | 0 | 0 | 0 | 0 | — | 0 | 0 | 1 | 1 | 3 | 3 |
| 34 | 2 | 5.6 | 0 | 1 | 1 | 2 | 3 | 0 | 3 | 0 | 1 | — | 3 | 0 | 3 | 3 | 3 | 3 |
| | 2 | 1.12 | 0 | 0 | 0 | 1 | 1 | 0 | 1 | 0 | 0 | — | 3 | 0 | 0 | 3 | 3 | 3 |
| | 2 | 0.28 | 0 | 1 | 0 | 0 | 0 | 0 | 0 | 0 | 0 | — | 0 | 0 | 0 | 0 | 3 | 3 |
| | 2 | 0.06 | 0 | 0 | 0 | 0 | 0 | 0 | 0 | 0 | 0 | — | 0 | 0 | 0 | 0 | 3 | 0 |
| 35 | 2 | 5.6 | 1 | 3 | 3 | 3 | 3 | 2 | 3 | 2 | 2 | 3 | 3 | 1 | 2 | 3 | 3 | 3 |
| | 2 | 1.12 | 0 | 1 | 2 | 3 | 3 | 1 | 1 | 0 | 1 | 3 | 3 | 1 | 1 | 3 | 3 | 3 |
| | 2 | 0.28 | 0 | 0 | 0 | 0 | 1 | 0 | 0 | 0 | 0 | 2 | 2 | 0 | 0 | 1 | 1 | 1 |
| 36 | 2 | 5.6 | 1 | 1 | 1 | 3 | 3 | 0 | 2 | 1 | 2 | 3 | 3 | 0 | 3 | 3 | 3 | 3 |
| | 2 | 1.12 | 0 | 1 | 0 | 3 | 1 | 0 | 3 | 1 | 0 | 3 | 2 | 0 | 3 | 3 | 3 | 3 |
| | 2 | 0.28 | 0 | 0 | 0 | 0 | 0 | 0 | 0 | 0 | 0 | 0 | 0 | 0 | 0 | 3 | 3 | 2 |

TABLE IIIA-continued

| Compound of Ex. No. | WAT* | kg/h | Pre-Emergent Plant Species | | | | | | | | | | | | | | |
|---|---|---|---|---|---|---|---|---|---|---|---|---|---|---|---|---|---|
| | | | L | M | N | O | P | B | Q | D | R | E | F | C | J | S | K | T |
| | 2 | 0.06 | 0 | 0 | 0 | 0 | 0 | 0 | 0 | 0 | 0 | 3 | 0 | 0 | 0 | 1 | 3 | 2 |
| | 2 | 0.01 | 0 | 0 | 0 | 0 | 0 | 0 | 0 | 0 | 0 | 3 | 1 | 0 | 0 | 0 | 2 | 2 |
| 37 | 2 | 5.6 | 1 | 2 | 3 | 3 | 3 | 0 | 3 | 1 | 2 | 3 | 3 | 2 | 3 | 3 | 3 | 3 |
| | 2 | 1.12 | 0 | 1 | 2 | 2 | 3 | 0 | 3 | 0 | 1 | 2 | 2 | 1 | 3 | 3 | 3 | 3 |
| | 2 | 0.28 | 0 | 0 | 2 | 2 | 3 | 0 | 3 | 0 | 0 | 1 | 1 | 0 | 3 | 3 | 3 | 3 |
| | 2 | 0.06 | 0 | 0 | 1 | 1 | 1 | 0 | 0 | 0 | 1 | 0 | 0 | 0 | 1 | 3 | 3 | 3 |
| | 2 | 0.01 | 0 | 0 | 0 | 0 | 0 | 0 | 0 | 0 | 0 | 0 | 0 | 0 | 0 | 0 | 2 | 1 |
| 38 | 2 | 5.6 | 1 | 3 | 3 | 3 | 3 | 0 | 3 | 0 | 3 | 3 | 3 | 0 | 3 | 3 | 3 | 3 |
| | 2 | 1.12 | 0 | 1 | 1 | 3 | 3 | 2 | 2 | 0 | 2 | 2 | 3 | 0 | 3 | 3 | 3 | 3 |
| | 2 | 0.28 | 1 | 1 | 0 | 3 | 2 | 1 | 3 | 0 | 2 | 3 | 2 | 0 | 2 | 3 | 3 | 3 |
| | 2 | 0.06 | 0 | — | 0 | 3 | 2 | 0 | — | 0 | 3 | 0 | 2 | 0 | 3 | 3 | 3 | 3 |
| | 2 | 0.01 | 0 | 0 | 0 | 0 | 0 | 0 | 0 | 0 | 0 | 0 | 0 | 0 | 0 | 1 | 1 | 2 |
| 39 | 2 | 5.6 | 2 | 2 | 3 | 3 | 3 | 0 | 3 | 2 | 3 | 3 | — | 1 | 3 | 3 | 3 | — |
| | 2 | 1.12 | 0 | 1 | 3 | 3 | 3 | 0 | 2 | 0 | 2 | 2 | — | 0 | 3 | 3 | 3 | — |
| | 2 | 0.28 | 1 | 1 | 1 | 3 | 3 | 0 | 0 | 0 | 2 | 1 | — | 0 | 3 | 3 | 3 | — |
| | 2 | 0.06 | 0 | 0 | 0 | 2 | 0 | 0 | 0 | 0 | 0 | 2 | — | 0 | 2 | 2 | 3 | — |
| | 2 | 0.01 | 0 | 0 | 0 | 0 | 0 | 0 | 0 | 0 | 2 | 0 | — | 0 | 0 | 0 | 1 | — |
| 40 | 2 | 5.6 | 1 | 2 | 3 | 3 | 3 | — | 1 | — | 2 | 3 | 3 | 1 | 3 | 3 | 3 | 3 |
| | 2 | 1.12 | 0 | 1 | 3 | 2 | 3 | — | 1 | — | 1 | 2 | 2 | 0 | 3 | 3 | 3 | 3 |
| | 2 | 0.28 | 0 | 1 | 1 | 2 | 1 | — | 0 | 0 | 0 | 1 | 1 | 0 | 3 | 3 | 3 | 3 |
| | 2 | 0.06 | 0 | 1 | 0 | 0 | 0 | — | 0 | — | 0 | 0 | 0 | 0 | 0 | 1 | 3 | 3 |
| | 2 | 0.01 | 0 | 0 | 0 | 0 | 0 | — | 0 | — | 0 | 0 | 0 | 0 | 0 | 0 | 2 | 0 |
| 41 | 2 | 5.6 | 0 | 2 | 3 | 3 | 3 | — | 2 | 3 | 2 | 3 | 3 | 1 | 3 | 3 | 3 | 3 |
| | 2 | 1.12 | 0 | 1 | 2 | 3 | 3 | — | 0 | 2 | 1 | 3 | 3 | 1 | 3 | 3 | 3 | 3 |
| | 2 | 0.28 | 0 | 0 | 1 | 1 | 1 | — | 0 | 1 | 0 | 3 | 2 | 0 | 2 | 3 | 3 | 3 |
| | 2 | 0.06 | 0 | 0 | 0 | 1 | 0 | — | 0 | 0 | 0 | 3 | 3 | 0 | 0 | 3 | 3 | 3 |
| | 2 | 0.01 | 0 | 0 | 0 | 0 | 0 | — | 0 | 0 | 0 | 0 | 0 | 0 | 0 | 0 | 1 | 0 |
| 49 | 2 | 5.6 | 0 | 3 | 2 | 3 | 3 | 0 | 2 | 2 | 2 | 2 | 2 | 1 | 3 | 3 | 3 | 3 |
| | 2 | 1.12 | 1 | 1 | 1 | 3 | 2 | 0 | 0 | 1 | 1 | 2 | 2 | 0 | 0 | 3 | 3 | 3 |
| | 2 | 0.28 | 0 | 1 | 0 | 2 | 0 | 0 | 0 | 0 | 0 | 1 | 1 | 0 | 0 | 3 | 3 | 3 |
| | 2 | 0.06 | 0 | 1 | 0 | 0 | 0 | 0 | — | 0 | 0 | 0 | 0 | 0 | 0 | 3 | 3 | 2 |
| | 2 | 0.01 | 0 | 2 | 0 | 0 | 1 | 0 | 0 | 0 | 0 | 2 | 2 | 0 | 0 | 1 | 3 | 3 |
| 50 | 2 | 5.6 | 2 | 2 | 3 | 3 | 3 | 1 | 2 | 2 | 2 | 3 | 3 | 1 | 3 | 3 | 3 | 3 |
| | 2 | 1.12 | 1 | 1 | 2 | 3 | 3 | 0 | 1 | 2 | 2 | 3 | 3 | 1 | 2 | 3 | 3 | 3 |
| | 2 | 0.28 | 0 | 1 | 1 | 3 | 3 | 0 | 0 | 1 | 0 | 2 | 3 | 1 | 2 | 3 | 3 | 3 |
| | 2 | 0.06 | 0 | 0 | 0 | 1 | 1 | 0 | 0 | 0 | 0 | 0 | 0 | 0 | 0 | 2 | 3 | 3 |
| | 2 | 0.01 | 0 | 0 | 0 | 1 | 0 | 0 | 0 | 0 | 1 | 0 | 0 | 0 | 0 | 2 | 2 | 1 |
| 51 | 2 | 5.6 | 1 | 1 | 3 | 3 | 3 | 0 | 1 | 1 | 2 | 3 | 3 | 0 | 3 | 3 | 3 | 3 |
| | 2 | 1.12 | 0 | 1 | 2 | 3 | 1 | — | 0 | 1 | 2 | 1 | 2 | 1 | 1 | 3 | 3 | 3 |
| | 2 | 0.28 | 0 | 0 | 0 | 2 | 0 | 0 | 0 | 0 | 3 | 0 | 1 | 0 | 0 | 3 | 3 | 3 |
| | 2 | 0.06 | 0 | 0 | 0 | 1 | 0 | 0 | 0 | 0 | 0 | 2 | 2 | 0 | 0 | 0 | 3 | 2 |
| 52 | 2 | 5.6 | 1 | 1 | 3 | 3 | 3 | — | 1 | 1 | 2 | 3 | 3 | 1 | 3 | 3 | 3 | 3 |
| | 2 | 1.12 | 0 | 1 | 3 | 3 | 1 | — | 1 | 1 | 1 | 3 | 3 | 1 | 1 | 3 | 3 | 3 |
| | 2 | 0.28 | 0 | 0 | 2 | 2 | 1 | — | 3 | 0 | 0 | 3 | 2 | 0 | 2 | 3 | 3 | 3 |
| | 2 | 0.06 | 0 | 1 | 0 | 2 | 0 | 0 | — | 0 | 0 | 0 | 1 | 0 | 1 | 2 | 3 | 3 |
| | 2 | 0.01 | 0 | 0 | 0 | 1 | 0 | 0 | 0 | 0 | 3 | 1 | 0 | 0 | 1 | 0 | 1 |
| 53 | 2 | 5.6 | 0 | 2 | 3 | 3 | 3 | — | 1 | 0 | 2 | 3 | 2 | 1 | 1 | 3 | 3 | 3 |
| | 2 | 1.12 | 0 | 1 | 2 | 3 | 2 | 0 | 0 | 0 | 1 | 1 | 3 | 0 | 0 | 3 | 3 | 3 |
| | 2 | 0.28 | 0 | 0 | 0 | 3 | 1 | — | 0 | 0 | 1 | 1 | 1 | 0 | 0 | 3 | 3 | 3 |
| | 2 | 0.06 | 0 | 1 | 0 | 0 | 0 | — | 0 | 0 | — | 1 | 2 | 0 | 0 | 1 | 2 | 2 |
| 54 | 2 | 5.6 | 1 | 2 | 3 | 3 | 3 | — | 1 | 1 | 1 | 3 | 3 | 1 | 3 | 3 | 3 | 3 |
| | 2 | 1.12 | 0 | 1 | 0 | 1 | 2 | 5 | 0 | 0 | 1 | 3 | 3 | 0 | 1 | 3 | 3 | 3 |
| | 2 | 0.28 | 0 | 0 | 0 | 1 | 1 | 0 | 0 | 0 | 0 | 0 | 3 | 0 | 0 | 3 | 3 | 3 |
| | 2 | 0.06 | 0 | 0 | 0 | 2 | 1 | — | 0 | 0 | 1 | 2 | 1 | 0 | 0 | 2 | 3 | 3 |
| 55 | 2 | 5.6 | 1 | 1 | 3 | 3 | 3 | — | 1 | — | 2 | 3 | 3 | 0 | 3 | 3 | 3 | 3 |
| | 2 | 1.12 | 1 | 1 | 0 | 3 | 3 | 0 | 1 | 0 | 0 | 1 | 0 | 0 | 3 | 3 | 3 | 3 |
| | 2 | 0.28 | 0 | 0 | 0 | 1 | 0 | — | 0 | — | 0 | 1 | 2 | 0 | 2 | 3 | 3 | 3 |
| | 2 | 0.06 | 1 | 0 | 0 | 0 | 0 | — | 0 | 0 | 0 | 1 | 1 | 0 | 0 | 2 | 3 | 1 |
| 56 | 2 | 5.6 | 0 | 1 | 2 | 2 | 2 | — | 0 | 2 | 2 | 3 | 1 | 0 | 3 | 3 | 3 | 3 |
| | 2 | 1.12 | 0 | 0 | 0 | 1 | 0 | — | 0 | — | 0 | 1 | 1 | 0 | 1 | 3 | 3 | 3 |
| | 2 | 0.28 | 0 | 0 | 0 | 0 | 0 | — | 0 | 0 | 0 | 0 | 1 | 0 | 0 | 1 | 2 | 2 |
| 2 | 2 | 5.6 | 3 | 3 | 3 | 3 | 3 | 3 | 3 | 3 | 3 | 3 | 3 | 3 | 3 | 3 | 3 | 3 |
| | 2 | 1.12 | 3 | 3 | 3 | 3 | 3 | 3 | 3 | 3 | 3 | 3 | 3 | 1 | 3 | 3 | 3 | 3 |
| | 2 | 0.28 | 3 | 3 | 3 | 3 | 3 | 1 | 1 | 3 | 3 | 3 | 3 | 1 | 3 | 3 | 3 | 3 |
| | 2 | 0.06 | 1 | 2 | 1 | 3 | 1 | 3 | 0 | 3 | 1 | 3 | 3 | 0 | 3 | 3 | 3 | 3 |
| | 2 | 0.01 | 1 | 1 | 0 | 1 | 0 | 0 | 0 | 1 | 5 | 1 | 0 | 0 | 3 | 3 | 3 | 3 |
| | 2 | 0.006 | 1 | 1 | 0 | 1 | 0 | 1 | 0 | 3 | 1 | 2 | 1 | 0 | 3 | 3 | 3 | 3 |
| 3 | 2 | 5.6 | 3 | 3 | 3 | 3 | 3 | 3 | 3 | 3 | 3 | 3 | 3 | 1 | 3 | 3 | 3 | 3 |
| | 2 | 1.12 | 3 | 2 | 3 | 3 | 3 | 3 | 2 | 3 | 3 | 3 | 3 | 1 | 3 | 3 | 3 | 3 |
| | 2 | 0.28 | 0 | 2 | 3 | 3 | 3 | 3 | 1 | 2 | 1 | 1 | 1 | 1 | 3 | 3 | 3 | 3 |
| | 2 | 0.06 | 0 | 1 | 1 | 3 | 1 | 0 | 0 | 0 | 0 | 3 | 3 | 0 | 3 | 3 | 3 | 3 |
| | 2 | 0.01 | 0 | 1 | 2 | 3 | 1 | 0 | 0 | — | — | 3 | 1 | 0 | 3 | 3 | 3 | 3 |
| | 2 | 0.006 | 0 | 1 | 0 | 2 | 1 | 0 | 0 | 0 | 1 | 1 | 1 | 0 | 3 | 3 | 3 | 3 |
| 4 | 2 | 5.6 | 3 | 3 | 3 | 3 | 3 | 1 | 1 | 3 | 1 | 3 | 3 | 1 | 3 | 3 | 3 | 3 |
| | 2 | 1.12 | 2 | 3 | 3 | 3 | 3 | 1 | 1 | 3 | 3 | 3 | 3 | 1 | 3 | 3 | 3 | 3 |
| | 2 | 0.28 | 1 | 3 | 1 | 2 | 3 | 0 | 0 | 3 | 0 | 3 | 2 | 1 | 3 | 3 | 3 | 3 |
| | 2 | 0.06 | 1 | 1 | 2 | 2 | 2 | 0 | 0 | 3 | 3 | 3 | 3 | 0 | 3 | 3 | 3 | 3 |
| | 2 | 0.01 | 1 | 1 | 0 | 1 | 1 | 0 | 0 | 2 | 1 | 3 | 1 | 0 | 2 | 3 | 3 | 3 |

TABLE IIIA-continued

| Compound of Ex. No. | WAT* | kg/h | Pre-Emergent Plant Species |||||||||||||||
|---|---|---|---|---|---|---|---|---|---|---|---|---|---|---|---|---|---|
| | | | L | M | N | O | P | B | Q | D | R | E | F | C | J | S | K | T |
| | 2 | 0.006 | 0 | 1 | 0 | 0 | 0 | 0 | 0 | 0 | 3 | 0 | 0 | 0 | 1 | 2 | 3 | 3 |
| 5 | 2 | 5.6 | 2 | 3 | 3 | 3 | 3 | 3 | 2 | 3 | 2 | 3 | 3 | 1 | 3 | 3 | 3 | 3 |
| | 2 | 1.12 | 2 | 2 | 3 | 3 | 3 | 0 | 3 | 3 | 3 | 3 | 3 | 1 | 3 | 3 | 3 | 3 |
| | 2 | 0.28 | 1 | 3 | 2 | 3 | 3 | 1 | 0 | 3 | 3 | 3 | 2 | 0 | 3 | 3 | 3 | 3 |
| | 2 | 0.06 | 1 | 1 | 0 | 3 | 2 | — | 0 | 3 | 1 | 3 | 0 | 0 | 3 | 3 | 3 | 3 |
| | 2 | 0.01 | 1 | 1 | 0 | 0 | 0 | 0 | — | 1 | 0 | 2 | 0 | 0 | 0 | 3 | 3 | 3 |
| | 2 | 0.006 | 1 | 1 | 2 | 0 | 0 | 0 | 0 | 0 | 1 | 0 | 0 | 0 | 3 | 3 | 3 | 3 |
| 65 | 2 | 5.6 | 1 | 2 | 3 | 3 | 3 | 3 | 1 | 3 | 3 | 3 | 3 | 0 | 3 | 3 | 3 | 3 |
| | 2 | 1.12 | 1 | 1 | 3 | 3 | 2 | 3 | 1 | 1 | 3 | 3 | 3 | 0 | 3 | 3 | 3 | 3 |
| | 2 | 0.28 | 0 | 1 | 3 | 3 | 1 | 0 | 0 | 0 | 2 | 2 | 3 | 0 | 3 | 3 | 3 | 3 |
| | 2 | 0.06 | 0 | 0 | 0 | 3 | 1 | 0 | 0 | 1 | 3 | 0 | 0 | 0 | 3 | 3 | 3 | 3 |
| | 2 | 0.01 | 0 | 0 | 0 | 0 | 0 | 0 | 0 | 0 | 3 | 0 | — | 0 | 0 | 0 | 1 | 1 |
| 66 | 2 | 5.6 | 2 | 2 | 3 | 3 | 3 | 0 | 3 | 3 | 3 | 3 | 3 | 1 | 3 | 3 | 3 | 3 |
| | 2 | 1.12 | 1 | 2 | 2 | 3 | 3 | — | 3 | 1 | 1 | 3 | 3 | 0 | 3 | 3 | 3 | 3 |
| | 2 | 0.28 | 1 | 2 | 0 | 2 | 3 | 0 | 0 | 1 | — | 3 | 3 | 0 | 3 | 3 | 3 | 3 |
| | 2 | 0.06 | 1 | 1 | 0 | 2 | 1 | 0 | 0 | 0 | — | 3 | 3 | 0 | 3 | 3 | 3 | 3 |
| | 2 | 0.01 | 1 | 1 | 1 | 2 | 1 | 0 | 0 | 2 | 0 | 1 | 1 | 0 | 2 | 3 | 3 | 3 |
| | 2 | 0.006 | 0 | 0 | 0 | 2 | 0 | — | 0 | 3 | 1 | 1 | 1 | 0 | 1 | 3 | 3 | 3 |
| | 2 | 0.001 | 0 | 1 | 0 | 1 | 0 | — | 0 | 3 | 0 | 1 | 0 | 0 | 1 | 3 | 3 | 3 |
| 67 | 2 | 5.6 | 3 | 3 | 3 | 3 | 3 | 2 | 2 | 3 | 3 | 3 | 3 | 1 | 3 | 3 | 3 | 3 |
| | 2 | 1.12 | 1 | 2 | 3 | 3 | 3 | 1 | 1 | 3 | 3 | 3 | 3 | 0 | 3 | 3 | 3 | 3 |
| | 2 | 0.28 | 1 | 2 | 2 | 3 | 1 | 0 | 0 | 2 | — | 3 | 3 | 0 | 3 | 3 | 3 | 3 |
| | 2 | 0.06 | 1 | 1 | 0 | 1 | 1 | — | 0 | 2 | — | 0 | 0 | 0 | 3 | 3 | 3 | 3 |
| | 2 | 0.01 | 0 | 0 | 0 | 0 | 0 | — | 0 | 0 | — | 0 | 1 | 0 | 3 | 3 | 3 | 3 |
| | 2 | 0.006 | 1 | 1 | 0 | 1 | 0 | 0 | 0 | 0 | 1 | 0 | 0 | 1 | 3 | 3 | 3 | 3 |
| | 2 | 0.001 | 0 | 0 | 0 | 0 | 0 | 0 | 3 | 0 | 0 | 0 | 0 | 1 | 3 | 3 | 3 | 3 |
| 47 | 2 | 5.6 | 1 | 2 | 3 | 3 | 3 | 0 | 1 | 3 | 3 | 3 | 3 | 1 | 3 | 3 | 3 | 3 |
| | 2 | 1.12 | 1 | 2 | 2 | 3 | 3 | 2 | 1 | 3 | 2 | 3 | 1 | 0 | 3 | 3 | 3 | 3 |
| | 2 | 0.28 | 0 | 1 | 1 | 2 | 1 | 0 | 0 | 3 | 3 | 0 | 0 | 0 | 3 | 3 | 3 | 3 |
| | 2 | 0.06 | 0 | 1 | 0 | 2 | 0 | 0 | 0 | 0 | 0 | 0 | 0 | 0 | 2 | 3 | 3 | 3 |
| | 2 | 0.01 | 0 | 1 | 0 | 0 | 0 | 0 | 0 | 0 | — | 1 | 0 | 0 | 0 | 2 | 3 | 3 |

*Weeks after treatment

TABLE IIIB

| Compound of Ex. No. | WAT* | kg/h | Post-Emergent Plant Species |||||||||||||||
|---|---|---|---|---|---|---|---|---|---|---|---|---|---|---|---|---|---|
| | | | L | M | N | O | P | B | Q | D | R | E | F | C | J | S | K | T |
| 20 | 2 | 5.6 | 0 | 0 | 1 | 1 | 0 | 1 | 0 | 0 | 1 | 0 | 1 | 1 | 0 | 1 | 2 | 1 |
| | 2 | 1.12 | 0 | 0 | 1 | 1 | 0 | 0 | 0 | 0 | 0 | 0 | 1 | 0 | 0 | 0 | 1 | 1 |
| 37 | 2 | 5.6 | 0 | 1 | 1 | 0 | 0 | 1 | 0 | 0 | 1 | 4 | 4 | 1 | 0 | 0 | 2 | 2 |
| 52 | 2 | 5.6 | 1 | 2 | 1 | 0 | 0 | 1 | 1 | 1 | 1 | 2 | 2 | 0 | 1 | 1 | 3 | 3 |
| | 2 | 1.12 | 0 | 0 | 0 | 0 | 0 | 0 | 1 | 0 | 0 | 0 | 0 | 0 | 0 | 0 | 3 | 1 |
| 54 | 2 | 5.6 | 1 | 1 | 1 | 0 | 0 | 1 | 1 | 1 | 1 | 3 | 3 | 0 | 0 | 1 | 2 | 3 |
| | 2 | 1.12 | 1 | 0 | 0 | 0 | 0 | 0 | 0 | 1 | 0 | 0 | 0 | 2 | 0 | 2 | 1 | 1 |
| 55 | 2 | 5.6 | 1 | 2 | 0 | 2 | 1 | 1 | 2 | 1 | 1 | 2 | 3 | 1 | 1 | 2 | 3 | 2 |
| | 2 | 1.12 | 0 | 0 | 0 | 0 | 0 | — | 1 | 2 | 0 | 0 | 0 | 0 | 1 | 1 | 3 | 0 |
| 4 | 2 | 5.6 | 1 | 3 | 1 | 2 | 0 | 2 | 4 | 2 | 1 | 4 | 2 | 0 | 1 | 3 | 3 | 2 |
| | 2 | 1.12 | 1 | 1 | 1 | 0 | 0 | 0 | 2 | 0 | — | 2 | 1 | 0 | 0 | 0 | 1 | 1 |
| 65 | 2 | 5.6 | 1 | 2 | 1 | 1 | 0 | 5 | 3 | 2 | 2 | 3 | 3 | 1 | 1 | 3 | 3 | 2 |
| | 2 | 1.12 | 1 | 1 | 0 | 0 | 0 | 1 | 1 | 2 | — | 3 | 2 | 0 | 1 | 3 | 3 | 3 |
| | 2 | 0.28 | 1 | 1 | 0 | 0 | 0 | 2 | 1 | 2 | — | 4 | 4 | 0 | 0 | 3 | 3 | 2 |
| 67 | 2 | 5.6 | 1 | — | 0 | 0 | 1 | 2 | 4 | 2 | — | 4 | 4 | 0 | 2 | 2 | 3 | 3 |
| | 2 | 1.12 | 1 | 1 | 0 | 0 | 0 | 1 | 3 | 2 | 0 | 1 | 1 | 0 | 0 | 0 | 2 | 3 |

*Weeks after treatment

In order to illustrate unexpectedly superior properties of representative compounds of this invention vis-a-vis the N-(alkoxyethyl) homologs thereof disclosed in the above-mentioned U.S. Pat. Nos. 3,574,746 and 3,586,496, a series of direct comparisons were made in pre-emergence herbicidal tests under identical greenhouse conditions. In these tests the compared compounds differed only in the alkoxyalkyl moiety thereof. As a preliminary comment, it will be understood, of course, by those skilled in the art that in evaluating generic classes of compounds for biological properties, e.g., as a herbicide, while the species of one class may exhibit generally superior properties, e.g., with respect to crop safety and/or weed injury, there may be instances where certain species of the other compared class will on occasion exhibit greater crop safety and/or weed injury than its homologous counterpart in the generally superior class; some such instances will be noted in the discussion below of the comparative herbicidal data for the N-(alkoxymethyl)-2-haloacetamides of this invention and the corresponding N-(alkoxyethyl) homologs of the prior art.

In one series, representative compounds of each homologous series of acetamides were tested against weeds commonly associated with sugarbeets. In a comparison between the compound of Example 1 and its N-(methoxyethyl) homolog in sugarbeets and certain weeds, it was found that the compound of Example 1 exhibited 90% control of yellow foxtail at the exceptionally low rate of 0.02 kg/hectare (kg/h) whereas it required 0.14 kg/h to obtain the same control with the methoxyethyl compound. The compound of Example 1 exhibited 80% control of crabgrass at 0.04 kg/h, as opposed to more than 0.07 kg/h for the methoxyethyl compound. Eighty percent (80 %) control of blackgrass was obtained with a 0.07 kg/h rate of the compound of Example 1, whereas it required 0.56 kg/h of the methoxyethyl homolog to obtain the same control. In another comparative test, the compound of Example 10 and its N-(ethoxymethyl) homolog were generally similar in crop safety, and injury to wild oats, barnyardgrass and blackgrass while the latter compound was slightly more selective in crabgrass and yellow foxtail.

In a comparison between the compound of Example 12 and its N-(isobutoxyethyl) homolog in sugarbeets, the former compound was shown to be safe at application rates up to at least 1.12 kg/h (the upper limit tested) while controlling wild oats at the same rate, black grass at 0.28 kg/h, and barnyardgrass, crabgrass and yellow foxtail at the still lower rate of 0.14 kg/h. In contrast, the isobutoxyethyl compound began to lose its safety in sugarbeets at below 0.56 kg/h and required the same rate to obtain 80% control of black grass, although control of barnyardgrass, crabgrass and yellow foxtail was also obtained of barnyardgrass, crabgrass and yellow foxtail was also obtained at 0.14 kg/h. Neither the N-(n-butoxymethyl) compound of Example 13 nor its N-(n-butoxyethyl) counterpart exhibited selectivity in one test in this series with sugarbeets.

In a comparative test between the N-(n-propoxymethyl) compound of Example 15 and its N-(n-propoxyethyl) homolog, the former compound selectively controlled wild oats, barnyardgrass, crabgrass and yellow foxtail at 0.56 kg/h, but the latter compound, although slightly more active in crabgrass and foxtail at lower rates was not selective with respect to wild oats at any rate up to 1.12 kg/h.

In a final comparison, the N-(isopropoxymethyl) compound of Example 18 was found to be safe in sugarbeets up to 1.12 kg/h, whereas its N-(isopropoxyethyl) homolog was safe only up to 0.28 kg/h. The latter compound was selective in yellow foxtail at 0.14 kg/h, whereas the former compound was selective at rates above about 0.56 kg/h.

In a series of tests in sorghum, the compound of Example 1 was less selective than its N-(methoxyethyl) homolog which was selective in johnsongrass, crabgrass and yellow foxtail at 0.04 kg/h whereas the compound of Example 1 required a slightly higher rate of 0.06 kg/h for selective control of crabgrass and yellow foxtail and did not selectively control johnsongrass.

When the compound of Example 12 was compared against its N-(isobutoxyethyl) homolog in sorghum, the latter compound was unsafe on that crop at the lowest rate tested, i.e., 0.14 kg/h, although the weeds johnsongrass, barnyardgrass, crabgrass and yellow foxtail were controlled at these rates. In contrast, the compound of Example 12 was safe on sorghum at rates above 0.28 kg/h while also controlling barnyardgrass, crabgrass and yellow foxtail at 0.14 kg/h and johnsongrass at 0.28 kg/h. In yet a further comparison between these two compounds against weeds commonly found in row crops, it was found that the compound of Example 12 controlled smartweed and hemp sesbania at 1.12 kg/h, whereas the N-isobutoxyethyl homolog did not control these weeds even at 2.24 kg/h, the highest rate in the test.

In yet another comparison, the N-(isopropoxymethyl) compound of Example 18 showed selectivity in sorghum with respect to barnyardgrass and yellow foxtail at rates as low as 0.14 kg/h and johnsongrass at 0.56 kg/h, whereas the N-(isopropoxyethyl) counterpart exhibited selectivity only with respect to barnyardgrass at 0.14 kg/h.

In comparative tests in rice, the N-(isobutoxymethyl) compound of Example 12 was selective at 0.02 kg/h whereas its N-(isobutoxyethyl) homolog was selective at the higher rate of 0.04 kg/h. The latter compound was safe on rice up to 0.14 kg/h, whereas the compound of Example 12 was unsafe above 0.04 kg/h.

In another comparative test, the N-(n-butoxymethyl) compound of Example 13 was compared with its N-(n-butoxyethyl) homolog against barnyardgrass in rice. The compound of Example 13 controlled barnyardgrass at 0.02 kg/h, while maintaining safety in rice up to about 0.14 kg/h. In contrast, the N-(butoxyethyl) homolog was unsafe on rice at rates above 0.07 kg/h and required 0.04 kg/h to control the barnyardgrass.

The N-(alkoxymethyl) compounds of Examples 10 and 15 and their N-(alkoxyethyl) homologs were of comparable selectivity in rice.

In comparative tests in wheat, the N-(methoxymethyl) compound of Example 1 and its N-(methoxyethyl) homolog both selectively controlled yellow foxtail at 0.07 kg/h and the latter compound also selectively controlled downy brome at 0.04 kg/h, but the former compound did not.

The comparative data for the N-(ethoxymethyl) compound of Example 10 and its N-(ethoxyethyl) homolog were indeterminate; the latter compound selectively controlled yellow foxtail and blackgrass at 0.14 kg/h, whereas the compound of Example 10 had a higher unit activity at this rate, controlling the same weeds, but also causing injury to the wheat; a lower test rate would have been required to determine the end point for crop injury for this compound.

The N-(isobutoxymethyl) compound of Example 12 and its N-(isobutoxyethyl) homolog both controlled yellow foxtail at 0.14 kg/h and had the same order magnitude of wheat safety.

The N-(n-butoxymethyl) compound of Example 13 and the N-(n-butoxyethyl) homolog both controlled blackgrass at 0.56 kg/h, but the compound of Example 13 also controlled yellow foxtail at the lower rate of 0.28 kg/h v. 0.50 kg/h for the homolog.

The N-(n-propoxyethyl) homolog of the N-(n-propoxymethyl) compound of Example 15 selectively controlled yellow foxtail and blackgrass at 0.14 kg/h, and had wheat safety at slightly over 0.28 kg/h, whereas the compound of Example 15 only selectively controlled yellow foxtail at 0.14 kg/h and was safe at slightly below 0.28 kg/h.

In yet another test, the compound of Example 18 was compared against its N-(isopropoxyethyl) homolog in wheat. The former compound controlled yellow foxtail at slightly less than 0.28 kg/h, whereas the N-(isopropoxyethyl) homolog was injurious to wheat at that rate and was only marginally safe at 0.14 kg/h, i.e., the lowest rate tested.

Additional tests were conducted to determine the comparative biological response of prior art N-alkoxyethyl-N-1-cycloalken-1-yl-2-haloacetamides and their N-alkoxymethyl homologs of this invention in both high organic matter soil (Drummer) and low organic matter soil (Ray silt loam). In these tests, the plant seeds were covered with either the Drummer or Ray soil and the test chemicals were applied to the soil surface and irrigated from overhead after treatment with the test chemical; subsequent watering was by subirrigation as necessary. The results are shown in Table IV. The N-(alkoxyethyl) compounds are identified by the letter B and the example numbers of the corresponding N-(alkoxymethyl) compound. For example, in the first comparison Compound B-1 is N-methoxyethyl-N-(1,2-dimethyl-1-cyclohexen-1-yl)-2-chloroacetamide, corresponding to the N-methoxymethyl homolog thereof described in Example 1. In the column titled "Soil Type" the Ray silt loam soil is identified by the letter "R" and the Drummer soil by the letter "D". The plants in the test were the same as those used in Tables IIIA and IIIB, hence the narrowleaf weeds were bromus tectorum, panicum spp., barnyardgrass and crabgrass and the broadleaf weeds were cocklebur, wild buckwheat, morningglory, hemp sesbania, lambsquarters, smartweed and velvet leaf. The average percent injury is shown for the crops individually and the narrowleaf and broadleaf weeds collectively.

for all species than the N-(alkoxyethyl) compounds, thus indicating a higher unit activity for the invention compounds. More particularly, the invention compounds are shown to be generally more active than the N-(alkoxyethyl) compounds, especially in the high organic matter Drummer soil at the lower, more economic rates of application.

The particular advantage of the invention compounds is best shown in 0.28 kg/h data against narrowleaf weeds in Drummer soil. But for the apparently anomalous data for the compounds of Example 1 and B-1 (note the greater injury to soybeans and narrowleaf weeds at 0.28 kg/h in Drummer soil than occurred with four times that amount of chemical at the 1.12 kg/h rate), the invention compounds showed generally superior weed control while maintaining crop safety in many instances. For example, in the comparative data for the compounds of Example 10 vs. B-10 at 0.28 kg/h in Drummer soil, the former compound controlled an

TABLE IV

| | | | Average Percent Injury | | | | | | | |
|---|---|---|---|---|---|---|---|---|---|---|
| | | | Crops | | | | | Weeds | | |
| Compound | Rate Kg/H | Soil type | Soybeans | Sugarbeets | Wheat | Rice | Sorghum | Narrow Leaf | Broad Leaf | All Species |
| Ex. 1 | 1.12 | R | 20 | 100 | 100 | 95 | 100 | 100 | 69 | 81 |
| B-1 | 1.12 | R | 30 | 85 | 100 | 95 | 95 | 98 | 63 | 76 |
| Ex. 1 | 1.12 | D | 15 | 50 | 75 | 20 | 50 | 97 | 56 | 62 |
| B-1 | 1.12 | D | 15 | 35 | 35 | 0 | 0 | 71 | 35 | 38 |
| Ex. 1 | 0.28 | R | 15 | 50 | 25 | 30 | 60 | 82 | 35 | 47 |
| B-1 | 0.28 | R | 10 | 30 | 75 | 35 | 15 | 90 | 45 | 52 |
| Ex. 1 | 0.28 | D | 0 | 60 | 0 | 0 | 0 | 85 | 32 | 39 |
| B-1 | 0.28 | D | 20 | — | 0 | 0 | 0 | 95 | 48 | 49 |
| Ex. 10 | 1.12 | R | 50 | 65 | 100 | 95 | 100 | 100 | 86 | 88 |
| B-10 | 1.12 | R | 80 | 50 | 100 | 95 | 100 | 100 | 64 | 79 |
| Ex. 10 | 1.12 | D | 10 | 65 | 95 | 95 | 100 | 100 | 72 | 79 |
| B-10 | 1.12 | D | 10 | 20 | 30 | 0 | 0 | 51 | 18 | 24 |
| Ex. 10 | 0.28 | R | 25 | 85 | 100 | 98 | 95 | 96 | 63 | 77 |
| B-10 | 0.28 | R | 30 | 25 | 90 | 65 | 98 | 98 | 52 | 66 |
| Ex. 10 | 0.28 | D | 10 | 60 | 80 | 0 | 40 | 91 | 57 | 60 |
| B-10 | 0.28 | D | 5 | 20 | 0 | 0 | 0 | 71 | 23 | 29 |
| Ex. 12 | 1.12 | R | 10 | 35 | 75 | 90 | 100 | 96 | 57 | 68 |
| B-12 | 1.12 | R | 0 | — | 40 | 25 | 100 | 100 | 38 | 56 |
| Ex. 12 | 1.12 | D | 0 | 40 | 30 | 25 | 75 | 91 | 41 | 52 |
| B-12 | 1.12 | D | 10 | 25 | 0 | 0 | 75 | 88 | 20 | 38 |
| Ex. 12 | 0.28 | R | 0 | 20 | 30 | 60 | 95 | 89 | 38 | 52 |
| B-12 | 0.28 | R | 0 | 20 | 30 | 20 | 55 | 66 | 7 | 27 |
| Ex. 12 | 0.28 | D | 0 | 20 | 50 | 10 | 30 | 87 | 27 | 41 |
| B-12 | 0.28 | D | 0 | 5 | 0 | 0 | 0 | 49 | 1 | 13 |
| Ex. 13 | 1.12 | R | — | — | — | — | — | — | — | — |
| B-13 | 1.12 | R | 10 | 15 | 50 | 0 | 98 | 79 | 24 | 41 |
| Ex. 13 | 1.12 | D | 10 | 20 | 10 | 0 | 50 | 86 | 43 | 46 |
| B-13 | 1.12 | D | 20 | 30 | 0 | 0 | 25 | 68 | 19 | 30 |
| Ex. 13 | 0.28 | R | 0 | 80 | 25 | 20 | 80 | 86 | 41 | 52 |
| B-13 | 0.28 | R | 0 | 5 | 40 | 20 | 95 | 81 | 36 | 46 |
| Ex. 13 | 0.28 | D | 5 | — | 0 | 0 | 60 | 94 | 53 | 55 |
| B-13 | 0.28 | D | 0 | 0 | 0 | 0 | 0 | 33 | 4 | 10 |
| Ex. 15 | 1.12 | R | 30 | 60 | 85 | 98 | 98 | 94 | 71 | 78 |
| B-15 | 1.12 | R | 20 | 50 | 100 | 80 | 100 | 95 | 68 | 76 |
| Ex. 15 | 1.12 | D | 15 | 50 | 15 | 10 | 40 | 98 | 60 | 59 |
| B-15 | 1.12 | D | 10 | 30 | 0 | 0 | 50 | 90 | 44 | 48 |
| Ex. 15 | 0.028 | R | 10 | 45 | 25 | 50 | 90 | 88 | 41 | 53 |
| B-15 | 0.028 | R | 20 | 20 | 100 | 40 | 100 | 87 | 46 | 60 |
| Ex. 15 | 0.028 | D | 10 | 30 | 5 | 25 | 50 | 88 | 39 | 47 |
| B-15 | 0.028 | D | 5 | 40 | 20 | 0 | 25 | 55 | 45 | 39 |
| Ex. 18 | 1.12 | R | 30 | 65 | 100 | 100 | 100 | 100 | 77 | 83 |
| B-18 | 1.12 | R | 20 | 70 | 100 | 90 | 98 | 93 | 53 | 70 |
| Ex. 18 | 1.12 | D | 20 | 75 | 15 | 25 | 50 | 98 | 57 | 61 |
| B-18 | 1.12 | D | 10 | 90 | 20 | 0 | 15 | 88 | 38 | 48 |
| Ex. 18 | 0.28 | R | 10 | 25 | 80 | 65 | 98 | 96 | 41 | 60 |
| B-18 | 0.28 | R | 5 | 25 | 20 | 25 | 100 | 90 | 37 | 50 |
| Ex. 18 | 0.28 | D | 0 | 20 | 0 | 0 | 5 | 89 | 40 | 41 |
| B-18 | 0.28 | D | 0 | 30 | 0 | 40 | 0 | 65 | 17 | 28 |

An analysis of the data in Table IV will show that in every comparison except that for the compounds of Example 1 vs. B-1 at 0.28 kg/h, the compounds of this invention resulted in an average higher percent injury average of 91% of the narrowleaf weeds and 57% of the broadleaf weeds with safety to soybeans and rice. In contrast, the Compound B-10 was less active against all plants, crops and weeds. Similarly, in the comparison of the compounds of Example 12 and B-12, the latter compound was less active against crops, but also against weeds, controlling only 49% of narrowleaf and 1% of broadleaf weeds, as opposed to 87% narrowleaf and 27% broadleaf control for the compound of Example 10, which showed safety in soybeans, sugarbeets and rice.

Where Compound B-13 showed only 33% narrowleaf control and 4% broadleaf control in Drummer soil at 0.28 kg/h, the compound of Example 13 exhibited 94% control of narrowleaf and 53% control of broadleaf weeds with no injury to wheat or rice and only 5% injury to soybeans. The same pattern of herbicidal activity was similarly demonstrated by the comparative data for the compounds of Examples 15 and 18 vis-a-vis compounds B-15 and B-18, respectively.

In still further comparative tests, field tests were conducted with the compounds of Examples 10 and 13 and their N-(alkoxyethyl) homologs, B-10 and B-13, respectively. The compounds of Examples 1 and 15 were included in these tests for comparative purposes. These tests were conducted in both high organic matter soil (Wabash silty clay loam) and low organic matter soil (Ray silt loam soil). The data from these tests are shown in Tables V-X; observations were made nineteen (19) days after treatment of the field plots with the test chemical. In Table V are shown the tolerances of the crops corn, sorghum, rice, wheat, sugarbeets, cotton, peanuts and soybeans to the amount (in kg/h) of chemical required to produce a 15% growth reduction, inhibition or injury of the crop plants; this tolerance is designated as the "$GR_{15}$" rate. In Table VI are shown the "$GR_{85}$" rates, i.e., the amount of herbicide required to produce an 85% growth reduction, inhibition or injury to the weed plants commonly associated with the above crops. The $GR_{15}$ and $GR_{85}$ rates are used as a measure of potential commercial performance, it being understood, of course, that suitable commercial herbicides may exhibit greater or lesser plant injuries within reasonable limits.

A further guide to the effectiveness of a chemical as a selective herbicide is the "selectivity factor" for a herbicide in given crops and weeds. The selectivity factor is expressed in terms of the $GR_{15}/GR_{85}$ ratio, i.e., the $GR_{15}$ rate for the crop divided by the $GR_{85}$ rate for the weed, both rates in kg/h. In Tables VII-X, respectively, are shown the selectivity factors for the given weeds vis-a-vis corn, soybeans, cotton and peanuts, the crops in which the invention compounds were particularly efficacious in these field tests. The weeds listed are those commonly associated with the particular crop. The symbol "NS" indicates "non-selective" and the symbol "IC" indicates "inconclusive" in these particular field tests. The plant species utilized in these tests are identified according to the following legend (maintaining, where applicable, the same legend for the same crop identified in earlier tables);

| a. Corn | G. Nutsedge (yellow) |
|---|---|
| P. Sorghum (grain) | d. Foxtail (green) |
| O. Rice | e. Wild oats |
| N. Wheat | f. Panicum (proso millet) |
| M. Sugarbeets | g. Barnyardgrass |
| b. Cotton | h. Jimsonweed |
| c. Peanuts | D. Morningglory |
| L. Soybeans | i. Pigweed (redroot) |
| I. Johnsongrass | j. Carpetweed |

In Tables V-X the symbols "R" and "W" represent the soil types Ray and Wabash silty clay loams, respectively.

TABLE V

| | | CROP TOLERANCE, $GR_{15}$ IN kg/H | | | | | | | |
|---|---|---|---|---|---|---|---|---|---|
| | Soil | | | | Crops | | | | |
| Compound | Type | a | P | O | N | M | b | c | L |
| Ex. 10 | R | 0.8 | 0.3 | <0.1 | <0.1 | 0.9 | 0.7 | 1.6 | 1.1 |
| | W | 0.9 | 0.2 | <0.1 | <0.1 | 0.5 | 0.9 | 1.9 | 1.2 |
| B-10 | R | 0.2 | 0.2 | <0.1 | <0.1 | 0.3 | 0.6 | 1.0 | 0.3 |
| | W | 0.6 | 0.2 | <0.1 | 0.1 | 0.6 | 0.7 | 1.2 | 0.5 |
| Ex. 13 | R | >4.5 | 1.2 | 0.3 | 0.3 | 3.1 | 3.7 | 4.4 | 4.3 |
| | W | 3.4 | 0.6 | 0.3 | 0.3 | 1.2 | 3.9 | >4.5 | 4.5 |
| B-13 | R | 2.1 | 0.7 | 0.7 | 0.3 | 2.7 | 4.3 | 4.5 | 4.5 |
| | W | 1.8 | 0.7 | 0.7 | 0.5 | 2.9 | >4.5 | >4.5 | 4.3 |
| Ex. 1 | R | 1.7 | 1.2 | 0.3 | 0.3 | 3.1 | 1.7 | 4.5 | >4.5 |
| | W | 2.2 | 0.6 | <0.3 | 0.3 | 2.7 | 0.9 | 3.5 | 2.0 |
| Ex. 15 | R | 2.1 | 0.3 | 0.1 | <0.1 | 0.5 | 2.1 | >4.5 | 2.1 |
| | W | 1.3 | 0.2 | 0.1 | 0.1 | 0.7 | 1.5 | >4.5 | 1.3 |

TABLE VI

| | | WEED CONTROL, $GR_{85}$ IN kg/H | | | | | | | |
|---|---|---|---|---|---|---|---|---|---|
| | Soil | | | | Weeds | | | | |
| Compound | Type | I | G | d | e | f | g | h | D | i | j |
| Ex. 10 | R | 0.9 | 0.6 | 0.2 | 0.9 | 0.6 | 0.1 | >4.5 | >4.5 | 2.6 | 3.7 |
| | W | 0.5 | 0.5 | 0.2 | 0.3 | 0.5 | 0.2 | 2.1 | >4.5 | 0.9 | 1.0 |
| B-10 | R | 0.2 | 0.5 | 0.3 | 0.6 | 0.6 | <0.1 | 2.0 | >4.5 | 1.3 | 1.8 |
| | W | 0.2 | 0.6 | 0.2 | 0.3 | 1.0 | 0.2 | 1.8 | >4.5 | 1.0 | 1.0 |
| Ex. 13 | R | 0.6 | 1.7 | 0.6 | 0.9 | 2.7 | 1.0 | >4.5 | >4.5 | 3.9 | >4.5 |
| | W | 0.7 | 1.7 | 0.5 | 1.1 | 0.9 | 0.3 | >4.5 | >4.5 | 1.1 | 1.8 |
| B-13 | R | 0.6 | 2.4 | 1.1 | 0.6 | 2.0 | 0.8 | >4.5 | >4.5 | 4.0 | 4.5 |
| | W | 0.7 | 2.4 | 0.5 | 1.7 | 2.2 | 0.3 | >4.5 | >4.5 | 3.4 | >4.5 |
| Ex. 1 | R | 4.3 | 3.1 | 0.6 | >4.5 | 1.0 | 0.5 | >4.5 | >4.5 | >4.5 | >4.5 |
| | W | 1.5 | 1.2 | 0.6 | 1.6 | 1.1 | 0.5 | >4.5 | >4.5 | 4.3 | 4.3 |
| Ex. 15 | R | 0.6 | 0.6 | 0.6 | 0.7 | 1.0 | 0.6 | 4.5 | >4.5 | 1.8 | 2.9 |

TABLE VI-continued

| | Soil | WEED CONTROL, GR₈₅ IN kg/H Weeds | | | | | | | | | |
|---|---|---|---|---|---|---|---|---|---|---|---|
| Compound | Type | I | G | d | e | f | g | h | D | i | j |
| | W | 0.5 | 0.6 | 0.3 | 0.6 | 0.8 | 0.2 | 2.7 | >4.5 | 0.8 | 0.9 |

TABLE VII

Selectivity of Tested Compounds in Corn and Associated Weeds

| Compound | Soil Type | I | G | d | e | f | g | h | D | i | j |
|---|---|---|---|---|---|---|---|---|---|---|---|
| Ex. 10 | R | NS | 1.3 | 4.0 | NS | 1.3 | 8.0 | NS | NS | NS | NS |
| | W | 1.8 | 1.8 | 4.5 | 3.0 | 1.8 | 4.5 | NS | NS | 1.0 | NS |
| B-10 | R | 1.0 | NS | NS | NS | NS | >2.0 | NS | NS | NS | NS |
| | W | 3.0 | 1.0 | 3.0 | 2.0 | NS | 3.0 | NS | NS | NS | NS |
| Ex. 13 | R | >7.5 | >2.6 | >7.5 | >5.0 | >1.7 | >4.5 | 1C | 1C | >1.2 | 1C |
| | W | 4.9 | 2.0 | 6.8 | 3.1 | 3.8 | 11.3 | NS | NS | 3.1 | 1.9 |
| B-13 | R | 3.5 | NS | 1.9 | 3.5 | 1.1 | 2.6 | NS | NS | NS | NS |
| | W | 2.6 | NS | 3.6 | 1.0 | NS | 6.0 | NS | NS | NS | NS |
| Ex. 1 | R | NS | NS | 2.8 | NS | 1.7 | 3.4 | NS | NS | NS | NS |
| | W | 1.4 | 1.7 | 3.4 | 1.3 | 2.0 | 4.4 | NS | NS | NS | NS |
| Ex. 15 | R | 3.5 | 3.5 | 3.5 | 3.0 | 2.1 | 3.5 | NS | NS | 1.2 | NS |
| | W | 2.6 | 2.2 | 4.3 | 2.2 | 1.6 | 6.5 | NS | NS | 1.6 | 1.4 |

TABLE VIII

Selectivity of Tested Compounds on Soybeans and Associated Weeds

| Compound | Soil Type | I | G | d | e | f | g | h | D | i | j |
|---|---|---|---|---|---|---|---|---|---|---|---|
| Ex. 10 | R | 1.2 | 1.8 | 5.5 | 1.2 | 1.8 | 11.0 | NS | NS | NS | NS |
| | W | 2.4 | 2.4 | 6.0 | 4.0 | 2.4 | 6.0 | NS | NS | 1.3 | 1.2 |
| B-10 | R | 1.5 | NS | 1.0 | NS | NS | >3.0 | NS | NS | NS | NS |
| | W | 2.5 | NS | 2.5 | 1.7 | NS | 2.0 | NS | NS | NS | NS |
| Ex. 13 | R | 7.2 | 2.5 | 7.2 | 4.8 | 1.6 | 4.3 | NS | NS | 1.1 | NS |
| | W | 6.4 | 2.6 | 9.0 | 4.1 | 5.0 | 15.0 | NS | IC | 4.1 | 2.5 |
| B-13 | R | 7.5 | 1.9 | 4.1 | 7.5 | 2.3 | 5.6 | IC | IC | 1.1 | IC |
| | W | 6.1 | 1.8 | 8.6 | 2.5 | 2.2 | 14.3 | IC | IC | 1.3 | NS |
| Ex. 1 | R | >1.1 | >1.5 | >7.5 | 1C | >4.5 | >9.0 | 1C | 1C | 1C | 1C |
| | W | 1.4 | 1.7 | 3.3 | 1.3 | 1.8 | 4.0 | NS | NS | NS | NS |
| Ex. 15 | R | 3.5 | 3.5 | 3.5 | 3.0 | 2.1 | 3.5 | NS | NS | 1.2 | NS |
| | W | 2.6 | 2.2 | 4.3 | 2.2 | 1.6 | 5.0 | NS | NS | 1.6 | 1.4 |

TABLE IX

Selectivity of Tested Compounds on Cotton and Associated Weeds

| Compound | Soil Type | I | G | f | g | h | D | i | j |
|---|---|---|---|---|---|---|---|---|---|
| Ex. 10 | R | NS | 1.0 | 1.2 | 7.0 | NS | NS | NS | NS |
| | W | 1.8 | 1.8 | 1.8 | 4.5 | NS | NS | IC | NS |
| B-10 | R | 3.0 | 1.2 | IC | >6.0 | NS | NS | NS | NS |
| | W | 3.5 | 1.2 | NS | 3.5 | NS | NS | NS | NS |
| Ex. 13 | R | 6.2 | 2.2 | 1.4 | 3.7 | NS | NS | NS | NS |
| | W | 5.6 | 2.3 | 4.3 | 13.0 | NS | NS | 3.5 | 2.2 |
| B-13 | R | 7.2 | 1.8 | 2.2 | 5.4 | NS | NS | 1.1 | NS |
| | W | 6.4 | 1.9 | 2.0 | 15.0 | IC | IC | 1.3 | IC |
| Ex. 1 | R | NS | NS | 1.7 | 3.4 | NS | NS | NS | NS |
| | W | NS | NS | NS | 1.8 | NS | NS | NS | NS |
| Ex. 15 | R | 3.5 | 3.5 | 2.1 | 3.5 | NS | NS | 1.2 | NS |
| | W | 3.0 | 2.5 | 1.9 | 7.5 | NS | NS | 1.9 | 1.7 |

TABLE X

Selectivity of Tested Compounds on Peanuts and Associated Weeds

| Compound | Soil Type | I | G | f | g | h | D | i | j |
|---|---|---|---|---|---|---|---|---|---|
| Ex. 10 | R | 1.8 | 2.7 | 2.7 | 16.0 | NS | NS | NS | NS |
| | W | 3.8 | 3.8 | 3.8 | 9.5 | NS | NS | 2.1 | 1.9 |
| B-10 | R | 5.0 | 2.0 | 2.0 | 10.0 | NS | NS | NS | NS |
| | W | 6.0 | 2.0 | 1.2 | 6.0 | NS | NS | 1.2 | 1.2 |
| Ex. 13 | R | 7.3 | 2.6 | 1.6 | 4.4 | NS | NS | 1.1 | NS |
| | W | >6.4 | >2.6 | >5.0 | >15.0 | IC | IC | >4.1 | >2.5 |
| B-13 | R | 7.7 | 1.9 | 2.3 | 5.6 | IC | IC | 1.1 | IC |
| | W | >6.4 | >1.9 | >2.0 | >15.0 | IC | IC | 1.3 | IC |
| Ex. 1 | R | 1.1 | 1.5 | 4.5 | 9.0 | IC | IC | IC | IC |
| | W | 2.3 | 2.9 | 3.2 | 7.0 | NS | NS | NS | NS |
| Ex. 15 | R | >7.5 | >7.5 | >4.5 | >22.5 | >1.7 | IC | >2.5 | >1.6 |
| | W | >9.0 | >7.5 | >5.6 | >22.5 | >1.7 | IC | >5.6 | >5.0 |

Since crop tolerance (Table V) and weed control (Table VI) are inter-related, a discussion of this relationship in terms of selectivity factors (Tables VII–X) is meaningful. In general, it is desirable that crop tolerance values be high, since higher concentrations of herbicide are frequently desired for one reason or another. Conversely, it is desirable that weed control rates be small for economical and possibly ecological reasons. However, small rates of application of a herbicide may not be adequate to control certain weeds, hence the best herbicides are those which control the greatest number of weeds with the greatest degree of crop safety. Accordingly, use is made of "selectivity factors" to quantify the relationship between crop safety and weed control. With reference to the selectivity factors listed in the tables, the higher the numerical value the greater selectivity of the herbicide for weed control in a given crop.

An analysis of the data in Tables V–X first with respect to the soil type indicates that, in general, herbicidal activity of the invention compounds is somewhat greater in the lower organic matter soil than in the higher organic soil, whereas the activity of the compared N-(alkoxyethyl) compounds is about the same, but slightly greater in the Wabash than in the Ray silty clay loam. The degree of difference of herbicidal activity in the two types of soil varies from plant to plant and compound to compound.

Referring to the comparative data in Table VII for selectivity of the tested compounds in corn, it will be seen that the selectivity factors for every weed in both types of soil is greater for the invention compounds of Examples 10 and 13 than those for the homologous prior art compounds B-10 and B-13, except for jimsonweed and morningglory (for which none of the compounds were selective in corn) and for johnsongrass (weed I) where the selectivity factor for B-10 was higher than that for the compound of Example 10. Additionally, the compound of Example 1 had higher selectivity factors than Compound B-10 in nutsedge (Wabash soil) foxtail, panicum and barnyardgrass and Compound B-13 in nutsedge and wild oats (Wabash soil), foxtail (Ray soil), panicum and barnyardgrass (Ray). The compound of Example 13 also had higher selectivity factors than Compound B-13 for every weed in Wabash soil and every weed in Ray soil, except johnsongrass and wild oats for which neither compound was selective. Moreover, the compound of Example 15 had higher selectivity factors than Compound B-10 in both types of soil in every weed in the test, except in jimsonweed and morningglory (weeds h and D, respectively) and in carpetweed (j) in Ray soil where both compounds were non-selective.

Referring now to comparative data in Table VIII for selectivity of the tested compounds in soybeans, it will be noted that, again, except for the non-selectivity of all tested compounds in jimsonweed and morningglory and for johnsongrass in Ray soil, the selectivity factors for the invention compound of Example 10 were in every instance higher than the prior art Compound B-10. Similarly, the compound of Example 13 had higher selectivity factors than Compound B-13 in every weed in Wabash soil and for nutsedge and foxtail in Ray soil. The compound of Example 1 also had higher selectivity factors than Compound B-10 in nutsedge, foxtail, panicum and barnyardgrass and B-13 in foxtail, panicum and barnyardgrass in Ray soil. Further, the compound of Example 15 had higher selectivity factors than Compound B-10 in both types of soil for every weed in the test, again excepting jimsonweed, morningglory and carpetweed in Ray soil (for which both compounds were non-selective). The selectivity factors for the compound of Example 15 were also higher than those for Compound B-15 in nutsedge, pigweed and carpetweed in Wabash soil.

Referring to Table IX containing comparative data for selectivity factors of associated weeds in cotton, it will be noted that the compound of Example 10 had higher selectivity factors than Compound B-10 in nutsedge and pigweed in Wabash soil and in panicum and barnyardgrass in both types of soil. The compound of Example 13 had higher selectivity factors than Compound B-13 in johnsongrass, panicum, barnyardgrass, pigweed and carpetweed in Wabash soil and in nutsedge in both types of soil. The compound of Example 1 had higher selectivity factors than Compound B-10 in panicum in Ray soil and in barnyardgrass in Wabash soil. The compound of Example 15 had higher selectivity factors than Compound B-10 in every weed in the test, except barnyardgrass in Ray soil, and in jimsonweed, morningglory in both soils and carpetweed in Ray soil for which weeds neither compound was selective. The compound of Example 15, likewise, had higher selectivity factors than Compound B-13 for panicum in Wabash soil and pigweed and panicum in both soils.

Finally, referring to the selectivity data for peanuts and associated crops, the data in Table X shows the compound of Example 10 to have higher selectivity factors than Compound B-10 in nutsedge, panicum and barnyardgrass in both Ray and Wabash soils and for pigweed and carpetweed in Wabash soil; both compounds were non-selective for jimsonweed and morningglory in both soils and for pigweed and carpetweed in Ray soil. The compound of Example 13 had higher selectivity factors than Compound B-13 for nutsedge in Ray soil and for johnsongrass, nutsedge, panicum, pigweed and carpetweed in Wabash soil. The compound of Example 1 had higher selectivity factors than Compound B-10 for panicum and barnyardgrass in both types of soil and for nutsedge in Wabash soil and Compound B-13 for panicum, nutsedge in Wabash soil and barnyardgrass in Ray soil. The compound of Example 15 was more selective than Compound B-10 for every weed in both types of soil, except for barnyardgrass in Ray soil and, questionably, in morningglory. The compound of Example 15 was also more selective than Compound B-13 in peanuts for every weed tested, except for johnsongrass (equivalent selectivity) and, again questionably, in morningglory.

The comparative data in the foregoing tables and discussion provides convincing evidence of the usefulness and unexpected and superior herbicidal activity performance of exemplary compounds of the invention vis-a-vis the most closely-related compounds of the prior art. The data also show the particular utility of the invention compounds as outstanding selective herbicides for grassy weeds and sedges in the important commercial crops such as corn, soybeans, cotton and peanuts, although also useful in other monocotyledonous and dicotyledonous crops and weeds.

The active ingredient herein can be admixed with one or more adjuvants which can be solid or liquid extenders, carriers, diluents, conditioning agents and the like to form herbidical compositions. Herbicidal compositions containing the active ingredients of this invention can be formulated with or in the form of granules, wettable powders, aqueous suspensions, dust formulations, emulsfiable oils and solutions in solvents. In general, these formulations can all contain one or more surface-active agents.

Surface-active agents which can be used in herbicidal formulations are well known to those skilled in the art and have been well documented in patents, bulletins and textbooks.

The preparation, formulation and particle size of the granules, wettable powders, aqueous suspensions, dusts, emulsifiable oils and solutions in solvents are also well known to those skilled in the art and well documented.

The active ingredient is usually present in the herbicidal compositions in a range of about 0.5 to 95 parts by weight per 100 parts by weight of wettable powder and dust formulations and from about 5 to 95 parts by weight per 100 parts by weight emulsifiable oil formulations. Formulations containing more or less than the above quantities of active ingredient can easily be prepared by those skilled in the art.

The quantity of active ingredient to be used in the field may vary within certain limits depending upon variables known to those in the art, e.g., condition of the soil, climate, plants, etc. In general, however, amounts ranging from about 0.02 to 11.2 or more kg/h should be adequate; a preferred range being from about 0.06 to 6.0 kg/h or suitably, an amount within the range of from 0.25 to 4.0 kg/h.

Although the compounds of this invention are primarily pre-emergence herbicides, post-emergence activity has also been demonstrated as shown in Tables IIB and IIIB.

Modes of application of the herbicidal compositions of this invention to the plant are well known to those skilled in the art. The application of liquid and particulate solid herbicidal formulations to the plant system or above-ground portions of plants can be carried out by conventional methods, e.g., power dusters, boom and hand sprayers and spray dusters.

The phytotoxic compositions of this invention can also contain other additaments, for example, fertilizers, safening agents, other phytotoxicants, pesticides and the like, used as adjuvant or in combination with any of the above-described adjuvants.

The compounds of this invention may be used in combination with known herbicides in order to provide enhanced biological effectiveness. The use of various herbicides in combination at the time of a single application or sequentially is common in practice. Herbicides which may be used in combination with the compounds of this invention include but are not limited to:

Substituted phenoxyaliphatic acids such as 2,4-dichlorophenoxyacetic acid; 2,4,5-trichlorophenoxyacetic acid, 2-methyl-4-chlorophenoxyacetic acid and the salts, esters and amides thereof; symmetrical or asymmetrical triazine derivatives, such as 2-chloro-4-ethylamino-6-isopropylamino-s-triazine; 2,4-bis(isopropylamino)-6-methoxy-s-triazine and 2-methylmercapto-4,6-bis(isopropylamino)-s-triazine; urea derivatives such as 3-(3,4-dichlorophenyl)-1,1-dimethylurea and 3-(m-trifluoromethylphenyl)-1,1-dimethylurea and 3-(3,4-dichlorophenyl)-1-methoxy-1-methylurea; pyridylium derivatives such as 1:1'-ethylene-2,2'-dipyridylium dihalide; acetanilides such as N-isopropyl-α-chloroacetanilide, and 2-chloro-2',6'-diethyl-N-methoxymethyl acetanilide; acetamides such as N,N-diallyl-α-chloroacetamide, N-alkoxyethyl-N-cycloalkenyl-α-haloacetamides, etc.; carbamates such as ethyl-N,N-di-n-propylthiolcarbamate, and 2,3-dichloroallyl diisopropylthiolcarbamate; substituted uracils such as 5-bromo-3-secbutyl-6-methyluracil, substituted anilines such as N,N-dipropyl-α,α,α-trifluoro-2,6-dinitro-p-toluidine; pyridazone derivatives such as 5-amino-4-chloro-2-phenyl-3-(2H)-pyridazinone; diphenyl ethers which may be unsubstituted or substituted with halogen, nitro, hydroxy, alkylthio, trifluoromethyl, cyano, alkyl, alkoxy, etc. groups; benzothiadiazinone derivatives such as 3-isopropyl-(1H)-benzo-2,1,3-thiadiazin-4-one-2,2-dioxide; N-(phosphonomethyl) glycine and its $C_{1-6}$ monoalkyl amine and alkali metal salts and combinations thereof in ratios of 1–4 lb/acre (1.12–4.48 kg/h) to 1–4 lb/acre of other herbicidal compounds, which may be selected from those exemplified above.

Combinations of various herbicidal compounds of this invention and isomeric mixtures thereof are clearly within the purview of this invention. For example, the isomeric mixture of the compounds of Examples 4 and 5 (which may be separated in accordance with the procedure shown in Example 6) and the isomeric mixture of the compounds of Examples 45 and 46 are excellent herbicides.

Fertilizers useful in combination with the active ingredients include, for example, ammonium nitrate, urea and superphosphate. Other useful additaments include materials in which plant organisms take root and grow such as compost, manure, humus, sand and the like.

While the illustrative embodiments of the invention have been described hereinbefore with particularity, it will be understood that various other modifications will be apparent to and can readily be made by those skilled in the art without departing from the scope and spirit of the invention. Accordingly, it is not intended that the scope of the claims appended hereto be limited to the examples and description set forth herein but rather the claims be construed as encompassing all the features of patentable novelty which reside in the present invention including all features which would be treated as equivalents thereof by those skilled in the art to which the invention pertains.

I claim:

1. Compounds having the formula

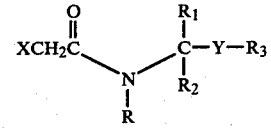

wherein
X is chlorine, bromine or iodine;
Y is O, S or —NH—;
R is a $C_{5-7}$ 1-cycloalken-1-yl radical which may be substituted with $C_{1-6}$ alkyl;
$R_1$ and $R_2$ are hydrogen or $C_{1-6}$ alkyl and
$R_3$ is $C_{1-6}$ alkyl, haloalkyl or alkoxyalkyl or alkenyl, haloalkenyl or alkynyl having up to 4 carbon atoms, cyclopropylmethyl, acetyl when Y is —NH— or pivaloyl or 2-cyanopropyl when Y is O.

2. Compounds according to claim 1 wherein R is a 1-cyclohexen-1yl radical.

3. Compounds according to claim 2 wherein said 1-cyclohexen-1-yl radical is substituted with a $C_{1-6}$ alkyl group on at least one of the ortho carbon atoms relative to the amide nitrogen atom.

4. Compounds according to claim 3 wherein X is chlorine, Y is S, $R_1$, $R_2$ and $R_3$ are $C_{1-6}$ alkyl groups.

5. Compunds according to claim 3, wherein X is chlorine, Y is NH, $R_1$ and $R_2$ are hydrogen and $R_3$ is acetyl.

6. Compounds according to claim 3 wherein X is chlorine, Y is O and $R_1$ and $R_2$ are hydrogen.

7. Compounds according to claim 6 wherein $R_3$ is $C_{1-6}$ alkyl or haloalkyl.

8. Compounds according to claim 6 wherein $R_3$ is alkenyl or haloalkenyl having up to 4 carbon atoms.

9. Compounds according to claim 6 wherein $R_3$ is propargyl alkynyl.

10. Compounds according to claim 6 wherein $R_3$ is $C_{1-6}$ alkoxyalkyl.

11. Compounds according to claim 6 wherein $R_3$ is cyclopropylmethyl.

12. Compound according to claim 7 which is N-(methoxymethyl)-N-(2,6-dimethyl-1-cyclohexen-1-yl)-2-chloroacetamide.

13. Compound according to claim 7 which is N-(ethoxymethyl)-N-(2,6-dimethyl-1-cyclohexen-1-yl)-2-chloroacetamide.

14. Compound according to claim 7 which is N-(ethoxymethyl)-N-(2-methyl-6-ethyl-1-cyclohexen-1-yl)-2-chloroacetamide.

15. Compound according to claim 7 which is N-(ethoxymethyl)-N-(2-ethyl-6-methyl-1-cyclohexen-yl)-2-chloroacetamide.

16. Compound according to claim 7 which is N-(isobutoxymethyl)-N-(2,6-dimethyl-1-cyclohexen-1-yl)-2-chloroacetamide.

17. Compound according to claim 7 which is N-(butoxymethyl)-N-(2,6-dimethyl-1-cyclohexen-1-yl)-2-chloroacetamide.

18. Compounds according to claim 1 wherein R is a 1-cyclopenten-1-yl radical, $R_1$ and $R_2$ are hydrogen, $R_3$ is $C_{1-6}$ alkyl and Y is O.

19. Compounds according to claim 18 wherein said 1-cyclopenten-1-yl radical is substituted with $C_{1-6}$ alkyl group on at least one of the carbon atoms ortho to the amide nitrogen.

20. Compound according to claim 19 which is N-(ethoxymethyl)-N-(2,5-dimethyl-1-cyclopenten-1-yl)-2-chloroacetamide.

21. Compound according to claim 19 which is N-(n-propoxymethyl)-N-(2,5-dimethyl-1-cyclopenten-1-yl)-2-chloroacetamide.

22. Herbicidal compositions comprising a herbicidally-effective amount of a compound having the formula $$\underset{R}{\underset{|}{\underset{N}{XCH_2C}}}\overset{O}{\underset{}{\overset{\|}{\diagdown}}}\overset{R_1}{\underset{R_2}{\overset{|}{\diagup}}}C-Y-R_3$$

wherein
X is chlorine, bromine or iodine;
Y is O, S or —NH—;
R is a $C_{5-7}$ 1-cycloalken-1-yl radical which may be substituted with $C_{1-6}$ alkyl;
$R_1$ and $R_2$ are hydrogen or $C_{1-6}$ alkyl and
$R_3$ is $C_{1-6}$ alkyl, haloalkyl or alkoxyalkyl or alkenyl, haloalkenyl or alkynyl having up to 4 carbon atoms, cyclopropylmethyl, acetyl when Y is —NH— or pivaloyl or 2-cyanopropyl when Y is O.

23. Compositions according to claim 22 wherein R is a 1-cyclohexen-1-yl radical.

24. Compositions according to claim 23 wherein said 1-cyclohexen-1-yl radical is substituted with a $C_{1-6}$ alkyl group on at least one of the ortho carbon atoms relative to the amide nitrogen atom.

25. Composition according to claim 24 wherein said compound is N-(methoxymethyl)-N-(2,6-dimethyl-1-cyclohexen-1-yl)-2-chloroacetamide.

26. Composition according to claim 24 wherein said compound is N-(ethoxymethyl)-N-(2,6-dimethyl-1-cyclohexen-1-yl)-2-chloroacetamide.

27. Composition according to claim 24 wherein said composition is a mixture of N-(ethoxymethyl)-N-(2-methyl-6-ethyl-1-cyclohexen-1-yl)-2-chloroacetamide and N-(ethoxymethyl)-N-(2-ethyl-6-methyl-1-cyclohexen-1-yl)-2-chloroacetamide.

28. Composition according to claim 24 wherein said compound is N-(isobutoxymethyl)-N-(2,6-dimethyl-1-cyclohexen-1-yl)-2-chloroacetamide.

29. Composition according to claim 24 wherein said compound is N-(butoxymethyl)-N-(2,6-dimethyl-1-cyclohexen-1-yl)-2-chloroacetamide.

30. Compositions according to claim 22 wherein R is a 1-cyclopenten-1-yl radical, $R_1$ and $R_2$ are hydrogen, $R_3$ is a $C_{1-6}$ alkyl and Y is O.

31. Compositions according to claim 30 wherein said 1-cyclopenten-1-yl radical is substituted with a $C_{1-6}$ alkyl group on at least one carbon atom ortho to the amide nitrogen atom.

32. Composition according to claim 31 wherein said compound is N-(ethoxymethyl)-N-(2,5-dimethyl-1-cyclopenten-1-yl)-2-chloroacetamide.

33. Composition according to claim 31 wherein said compound is N-(n-propoxymethyl)-N-(2,5-dimethyl-1-cyclopenten-1-yl)-2-chloroacetamide.

34. Method for controlling undesirable plants associated with monocotyledonous and dicotyledonous crop plants which comprises applying to the locus of said plants a herbicidally-effective amount of a compound having the formula $$\underset{R}{\underset{|}{\underset{N}{XCH_2C}}}\overset{O}{\underset{}{\overset{\|}{\diagdown}}}\overset{R_1}{\underset{R_2}{\overset{|}{\diagup}}}C-Y-R_3$$

wherein
X is chlorine, bromine or iodine;
Y is O, S or —NH—;
R is $C_{5-7}$ 1-cycloalken-1-yl radical which may be substituted with $C_{1-6}$ alkyl;
$R_1$ and $R_2$ are hydrogen or $C_{1-6}$ alkyl and
$R_3$ is $C_{1-6}$ alkyl, haloalkyl or alkoxyalkyl or alkenyl, haloalkenyl or alkynyl having up to 4 carbon atoms, cyclopropylmethyl, acetyl when Y is —NH— or pivaloyl or 2-cyanopropyl when Y is O.

35. Method according to claim 34 wherein R is a 1-cyclohexen-1-yl radical.

36. Method according to claim 35 wherein said 1-cyclohexen-1-yl radical is substituted with a $C_{1-6}$ alkyl group 37. Method according to claim 36 wherein said compound is N-(methoxymethyl)-N-(2,6-dimethyl-1-cyclohexen-1-yl)-2-chloroacetamide.

38. Method according to claim 36 wherein said compound is (ethoxymethyl)-N-(2,6-dimethyl-1-cyclohexen-1-yl)-2-chloroacetamide.

39. Method according to claim 36 wherein said composition is a mixture of N-(ethoxymethyl)-N-(2-methyl-6-ethyl-1-cyclohexen-1-yl)-2-chloroacetamide and N-(ethoxymethyl)-N-(2-ethyl-6-methyl-1-cyclohexen-1-yl)-2-chloroacetamide.

40. Method according to claim 36 wherein said compound is N-(propoxymethyl)-N-(2,6-dimethyl-1-cyclohexen-1-yl)-2-chloroacetamide.

41. Method according to claim 36 wherein said compound is N-(butoxymetyl)-N-(2,6-dimethyl-1-cyclohexen-1-yl)-2-chloroacetamide.

42. Method according to claim 34 wherein R is a 1-cyclopenten-1-yl radical, $R_1$ and $R_2$ are hydrogen, $R_3$ is a $C_{1-6}$ alkyl and Y is O.

43. Method according to claim 42 wherein said 1-cyclopenten-1-yl radical is substituted with a $C_{1-6}$ alkyl radical in at least one ortho position relative to the amide nitrogen atom.

44. Method accordig to claim 43 wherein said compound is N-(ethoxymethyl)-N-(2,6-dimethyl-1-cyclopenten-1-yl)-2-chloroacetamide.

45. Method according to claim 43 wherein said compound is N-(n-propoxymethyl)-N-(2,6-dimethyl-1-cyclopenten-1-yl)-2-chloroacetamide.

* * * * *